(12) United States Patent
Li et al.

(10) Patent No.: US 10,377,833 B2
(45) Date of Patent: Aug. 13, 2019

(54) BISPECIFIC ANTI-HER2 ANTIBODY

(71) Applicant: Beijing Mabworks Biotech Co. Ltd, Beijing (CN)

(72) Inventors: Feng Li, Beijing (CN); Boyan Zhang, Foster City, CA (US); Pei Ye, Lowarenceville, GA (US); Jian Zhao, Beijing (CN); Sijia Huang, Beijing (CN); Chunyang Jin, Beijing (CN)

(73) Assignee: Beijing Mabworks Biotech Co., Ltd., Beijing (CN)

( * ) Notice: Subject to any disclaimer, the term of this patent is extended or adjusted under 35 U.S.C. 154(b) by 66 days.

(21) Appl. No.: 15/656,390

(22) Filed: Jul. 21, 2017

(65) Prior Publication Data
US 2018/0022820 A1  Jan. 25, 2018

Related U.S. Application Data

(63) Continuation-in-part of application No. 15/461,732, filed on Mar. 17, 2017, now Pat. No. 9,745,382.

(30) Foreign Application Priority Data

Jul. 22, 2016 (CN) .......................... 2016 1 0584242

(51) Int. Cl.
  C12N 5/071 (2010.01)
  C07K 16/32 (2006.01)
  A61P 35/00 (2006.01)
  A61K 39/00 (2006.01)

(52) U.S. Cl.
  CPC .............. *C07K 16/32* (2013.01); *A61P 35/00* (2018.01); *A61K 2039/505* (2013.01); *C07K 2317/24* (2013.01); *C07K 2317/31* (2013.01); *C07K 2317/41* (2013.01); *C07K 2317/526* (2013.01); *C07K 2317/732* (2013.01); *C07K 2317/734* (2013.01); *C07K 2317/76* (2013.01); *C07K 2317/92* (2013.01); *C12N 5/0682* (2013.01)

(58) Field of Classification Search
  CPC ................................ C12N 5/06; C12N 5/0682
  See application file for complete search history.

(56) References Cited

U.S. PATENT DOCUMENTS

| 2015/0166654 A1* | 6/2015 | Igawa ................... C07K 16/005 530/387.3 |
| 2017/0073426 A1* | 3/2017 | Ohtomo ............. G01N 33/5011 |
| 2017/0321240 A1* | 11/2017 | Song ........................ C12N 5/00 |

FOREIGN PATENT DOCUMENTS

| CN | 105017421 A | 11/2015 |
| CN | 105307676 A | 2/2016 |
| WO | 8906692 A1 | 7/1989 |
| WO | 9222653 A1 | 12/1992 |
| WO | 2004008099 A2 | 1/2004 |
| WO | 2015/077891 A1 | 4/2015 |
| WO | 2015/077891 A1 | 6/2015 |
| WO | 2015091738 A1 | 6/2015 |
| WO | 2015/164665 A1 | 10/2015 |

OTHER PUBLICATIONS

Chan et al. (Biotechnol. J. Mar. 2016; 11 (3): 399-414).*
Haryadi et al. (Bioengineered. Mar.-Apr. 2013; 4 (2): 90-4).*
Zhang et al. (Glycobiology. Jul. 2012; 22 (7): 897-911).*
Yamane-Ohnuki et al. (Methods Mol. Biol. 2008; 435: 1-16).*
Lu et al. (J. Biol. Chem. Nov. 12, 2010; 285 (46): 36245-54).*
Kanda et al. (J. Biotechnol. Jun. 30, 2007; 130 (3): 300-10).*
Hellbusch et al. (J. Biol. Chem. Apr. 6, 2007; 282 (14): 10762-72).*
International Search Report dated Oct. 17, 2017 in International Application No. PCT/CN2017/093816.
Chan, et al., "Inactivation of GDP-fucose transporter gene (Slc35c1) in CHO cells by ZFNs, TALENs and CRISPR-Cas9 for production of fucose-free antibodies", Biotechnology Journal, vol. 11, Issue 3, Oct. 16, 2015, pp. 399-414.
Meng, Y., "Effective Suppression of Breast Tumor Growth by a Bispecific Antibody Targeting Distinct ErbB2 Epitopes", Chinese Master's Theses Full-text Database (Medicine and Health Sciences), May 15, 2014, 68 pages. (with English Abstract at pp. 3-4.).
Tang, et al., "Development of antibody drugs targeting against HER2 for cancer therapy", Acta Pharmaceutica Sinica 2012, No. 10, vol. 47, Oct. 12, 2012, pp. 1297-1305.
Fuentes et al., "Synergy between trastuzmab and pertuzumab for human epidermal growth factor 2 (Her2) from colocalization: an in silico based mechanism.", Breast Cancer Res. 13:R54, 2011, 9 pages.
Li et al., "Bispecific antibody to ErbB2 overcomes trastuzumab resistance through comprehensive blockage of ErbB2 heterodimerization.", Cancer Res 73 (21), 2013, pp. 6471-6483.
Mariuzza et al., "The Structural Basis of Antigen-Antibody Recognition", Annual Review of Biophysics and Biophysical Chemistry, vol. 16, Jun. 1987, pp. 139-159.
Rudikoff et al., "Single amino acid substitution altering antigen-binding specificity", Proc. Natl. Acad. Sci. USA, vol. 79, Mar. 1982, pp. 1979-1983.

(Continued)

*Primary Examiner* — Stephen L Rawlings
(74) *Attorney, Agent, or Firm* — Perkins Coie LLP; Viola T. Kung

(57) ABSTRACT

The present invention relates to humanized bispecific anti-HER2 antibodies that comprise one antigen binding site containing variable regions of heavy and light chain of trastuzumab, and another antigen binding site containing variable regions of heavy and light chain of pertuzumab. The bispecific anti-HER2 antibodies is effective for treating cancer, such as breast cancer, gastric cancer, or ovarian cancer. Preferred bispecific anti-HER antibodies of the present invention are afucosylated antibodies. The present invention also relates to Chinese Hamster ovary (CHO) mutant cell line that has a dysfunctional Slc35C1 gene, which is the only dysfunctional gene in the mutant that affects glycan regulation.

1 Claim, 15 Drawing Sheets

Specification includes a Sequence Listing.

(56) References Cited

OTHER PUBLICATIONS

Scheuer et al., "Strongly enhanced antitumor activity of trastuzumab and pertuzumab combination treatment on HER2-positive human xenograft tumor models.", Cancer Research 69(24), 2009, pp. 9330-9336.
Shinkawa et al., "The absence of fucose but not the presence of galactose or bisecting N-acetylglucosamine of human IgG1 complex-type oligosaccharides shows the critical role of enhancing antibody-dependent cellular cytotoxicity .", J Biol Chem 278(5), 2003, pp. 3466-3473.
Winkler et al., "Changing the antigen binding specificity by single point mutations of an anti-p24 (HIV-1) antibody", J Immunol, 165 (8), Oct. 15, 2000, pp. 4505-4514.
Zhang et al., "Combating HER2-overexpressing breast cancer through induction of calreticulin exposure by Tras-Permut CrossMab", Oncoimmunology 4(3), Mar. 2015, pp. e994391-e9943991-13.
Zhang et al., "Identification of functional elements of the GDP-fucose transporter SLC35C1 using a novel Chinese hamster ovary mutant", Glycobiology vol. 22 No. 7, Apr. 6, 2012, pp. 897-911.

\* cited by examiner

US 10,377,833 B2

BISPECIFIC ANTI-HER2 ANTIBODY

This application is a continuation-in-part of U.S. application Ser. No. 15/461,732, filed Mar. 17, 2017, now U.S. Pat. No. 9,745,382; which claims priority of Chinese Application No. 201610584242.9, filed Jul. 22, 2016. The above applications are incorporated by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Mar. 13, 2017, and a size of 30.7 kilobytes. The Sequence Listing filed via EFS-Web is part of the specification and is hereby incorporated in its entirety by reference herein.

TECHNICAL FIELD

The present invention pertains to the fields of oncology therapy and molecular immunology, and relates to an anti-Her2 antibody, and pharmaceutical compositions and uses thereof. In particular, the present invention relates to humanized bispecific anti-Her2 antibodies that comprise one antigen binding site containing variable regions of heavy and light chain of trastuzumab, and another antigen binding site containing variable regions of heavy and light chain of pertuzumab. The present invention also relates to Chinese Hamster ovary (CHO) mutant cell line that has a dysfunctional Slc35C1 gene; the mutant cell line expresses proteins having reduced fucosylation.

BACKGROUND OF THE INVENTION

Human epidermal growth factor receptor 2 (abbreviated as Her2, ERBB2, HER2/neu or c-erbB2) is a protein encoded by ERBB2 gene. In normal cells, Her2 has a very low expression level; but Her2 is highly expressed during the period of embryonic development, and is very important in the regulation of cell proliferation, differentiation, development, adhesion and migration (Gutierrez, C. and R. Schiff, HER2: biology, detection, and clinical implications. Arch Pathol Lab Med, 2011. 135(1): p. 55-62.).

Her2 belongs to the family of human epidermal growth factor receptor, and this family consists of 4 members: Her1 (EGFR), Her2, Her3 and Her4. Her2 has no specific ligand, and the activation of its downstream pathway depends on formation of homologous or heterologous dimers (Gutierrez et al, Arch Pathol Lab Med, 2011. 135(1): p. 55-62.). Human epidermal growth factors are all locate on cell surface, and have a similar structure: one extracellular domain (ECD) binding to a ligand, one single transmembrane α-helix transmembrane domain and one intracellular region that consists of an intracellular membrane-proximal domain, a tyrosine kinase catalytic domain and a tyrosine-rich C-terminal tail domain playing a regulatory role (Eccles, Int J Dev Biol, 2011. 55(7-9): p. 685-96). The extracellular domain (ECD) of human epidermal growth factor can further be separated into 4 subdomains, i.e., regions I, II, III and IV, in which regions II and IV are cysteine-rich domains and participate in dimerization and activation of the receptor.

Overexpression of Her2 may results in disorders of cell normal functions, and usually closely relates to tumor genesis and development. The homologous or heterologous polymerization of Her2 may lead to phosphorylation of tyrosine residues of the receptor, and initiate many signal pathways and causes cell proliferation and tumor genesis. As a biomarker for prognosis and prediction, amplification or overexpression of Her2 gene occurs in about 15-30% breast cancer and 10-30% gastric/esophageal cancer. Overexpression of Her2 may also be observed in other tumors such as ovary, endometrium, bladder, lung, colon, and head-neck tumors.

In breast cancer, Her2 is commonly recognized as a predictive factor and a therapeutic target. Since Her2 has no specific ligand, its antibodies usually inhibit tumor cells by blocking dimerization and activation of the receptor and mediating killing effect of immune system. At present, Trastuzumab and Pertuzumab are the main Her2-targeted therapeutic antibodies commercially available.

In 1998, FDA approved a Her2-targeting humanization monoclonal antibody, trastuzumab (also called as HERCEPTIN®; humanization degree 95%) of Genentech Inc. This antibody recognizes Her2 extracellular domain IV juxtamembrane epitope, and its antigen affinity constant can be up to 0.1 nmol/L. Trastuzumab recognizes the epitope consisting of the 3 loops (557-561, 570-573 and 593-603) at the C-terminal of section IV. Because the epitope may be close to or directly interact with the binding domain of its dimerization partner, trastuzumab's binding to the epitope may induce steric hindrance inhibiting the dimerization process. In addition, trastuzumab's binding may also protect the extracellular domain of the Her2 receptor from the attack by proteinase for hydrolysis.

The mechanisms of action of trastuzumab may include: immune-induced bioactivities (antibody dependent cell-mediated cytotoxicity (ADCC) and Natural killer cell activity), inducing the internalization of Her2 receptor, inhibiting DNA repair, breaking PI3K pathway, activating p27kip1 induced G1 cycle stoppage, stimulating cancer cell apoptosis and inhibiting the activation of intracellular p95 domain off of the extracellular domain of the receptor[4,5]. Among them, there have been reports about trastuzumab induced immuno-mediated therapeutic bioactivities. In particular, ADCC plays an important role, as it was shown in a BT474 xenograft mouse model, when the Fc receptor was knocked out, the inhibition rate of cancer growth was reduced from 96% to 29% (Nat Med, 2000, 6:443-6). Kohrt et al (J Clin Invest, 2012. 122(3): 1066-75) report that stimulation of natural killer cells with a CD137-specific antibody enhances trastuzumab efficacy in xenotransplant models of breast cancer.

Trastuzumab is currently used as a first-line drug for treatment of breast cancer, and is effective in treatment of metastatic breast cancer with Her2 overexpression, and its objective reflection rate of single drug first-line treatment is 30-50%; but it has unsatisfied effect in treating metastatic breast cancer with lower Her2 expression, and resistance has been developed in a number of patients for whom the antibody is initially effective within 1 year. This may be related to shielding of antigen epitopes or abnormal activation of receptor signaling pathway caused by changes of some gene expressions in tumor cells. In addition, Her2 together with other members (Her1, Her3 and Her4) of the family can form ligand-dependent or ligand-independent heterologous dimers, thereby activating downstream pathways, and then resulting proliferation of tumor cells, while trastuzumab cannot inhibit formation of heterologous dimers, so this may be one of reasons for the development of resistance.

Pertuzumab (PERJETA®) was approved by FDA for marketing in USA in 2012, and has certain curative effects on advanced prostate cancer, non-small cell lung cancer, ovarian cancer and breast cancer, but its curative effects still depend on Her2 expression level.

Pertuzumab recognizes key sites for heterologous dimerization of Her2 extracellular domain II, and the epitope recognized thereby are located in segment 245-311 of II subregion center, and key residues are H245, V286, S288, L295, H296 and K311. In which, L295, H296 are key sites for mediating heterologous dimerization of Her2 and Her3, and L295A/H296A double mutation can completely block heterologous dimerization of Her2/Her3 (Franklin, M. C., et al., Insights into ErbB signaling from the structure of the ErbB2-pertuzumab complex. Cancer Cell, 2004. 5(4): p. 317-28.). Hence, Pertuzumab can be used for effectively inhibiting the formation of Her2/Her3 heterologous dimer, but does not show obvious inhibition effects on the formation of EGFR/Her2 heterologous dimer.

At present, there is a need for developing new anti-HER2 antibodies.

DETAILED DESCRIPTION OF THE INVENTION

Definitions

Figure 1:
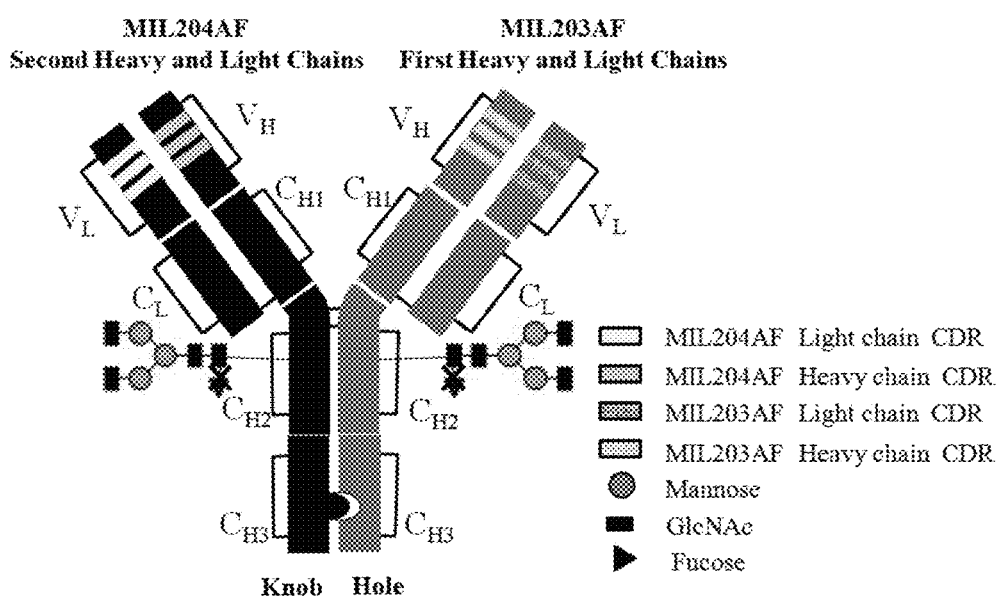
FIG. 1 shows the structure of a preferred embodiment of humanized bispecific anti-Her2 antibodies of the present invention.

As used herein, the term "about" refers to ±10% of the recited value.

As used herein, the term "an effective amount" refers to an amount to obtain or at least partially obtain a desired effect. An effective amount can be determined by a skilled technician in the art. For example, an effective amount for treatment use depends on severity of disease to be treated, general status of immune system of a patient, general status of a patient such as age, body weight and gender, administration method for drugs, and other therapies simultaneously applied.

As used herein, the term "adjuvant" refers to a non-specific immune enhancer, when it is delivered with an antigen, it can enhance immune response of a subject to the antigen or change type of immune response. There are many kinds of adjuvants, including but not being limited to aluminum adjuvants (e.g., aluminum hydroxide), Freund's adjuvants, lipopolysaccharides, and cell factors. Freund's adjuvants are the most popular adjuvants in animal tests at present, while aluminum hydroxide adjuvant is often used in clinical experiments.

As used herein, the term "antibody" refers to an immune globulin usually consisting of two pairs of polypeptide chains (each pair has a light (L) chain and a heavy (H) chain). The antibody light chain can be classified as κ light chain and λ light chain. The heavy chain can be classified as μ, δ, γ, α or ε, and isotypes of antibody are separately defined as IgM, IgD, IgG, IgA and IgE. In light chain and heavy chain, variable region and constant region are linked via "J" region with about 12 or more amino acids, and heavy chain further contains "D" region with about 3 or more amino acids. Each heavy chain consists of a heavy chain variable region ($V_H$) and heavy constant region ($C_H$). Heavy chain consists of 3 domains (CH1, CH2, and CH3). Each light chain consists of a light chain variable region ($V_L$) and a light chain constant region ($C_L$). The constant regions of antibody can mediate immune globulin to bind to host tissues or factors, including various cells (e.g., effector cells) of immune system and first component (C1q) of classical complement system. $V_H$ and $V_L$ regions can further be classified as high variability regions (called as complementary determining region (CDR)), in which relatively conservative regions called as framework regions (FR) are scattered. These $V_H$ and $V_L$ regions are composed of 3 CDR regions and 4 FR regions in order of: FR1, CDR1, FR2, CDR2, FR3, CDR3, FR4, from amino terminal to carboxyl terminal. Variable regions ($V_H$ and $V_L$) of each pair of heavy chain/light chain form an antibody binding site.

As used herein, "antibody-dependent cell-mediated cytotoxicity" (ADCC) is a mechanism of cell-mediated immune defense whereby an effector cell of the immune system actively lyses a target cell, whose membrane-surface antigens have been bound by specific antibodies.

As used herein, the term "antigen-binding fragment" of antibody refers to a polypeptide containing a fragment of full-length antibody, which remains ability of specifically binding to the same antigen to which the full-length antibody binds, and/or competes with the full-length antibody to specifically bind to antigen.

As used herein, the term "complement-dependent cytotoxicity" (CDC) is a function of the complement system. It is the processes in the immune system that kill pathogens by damaging their membranes without the involvement of antibodies or cells of the immune system.

As used herein, the term "core fucose" refers to a fucose linked to GlcNAC in connection with asparagine in N-saccharide core pentasaccharides.

As used herein, the term "EC50" refers to concentration for 50% of maximal effect, that is, a concentration that causes 50% of maximal effect.

As used herein, the term "FcγRIIIa" is a 50-70 kDa glycoprotein, belonging to Ig superfamily, having two C2 structures, and its gene is located at 1q23-24 of chromosome. FcγRIII binds to human IgG, IgG3, and is a low affinity receptor. FcγRIII comprises 2 allotypes, FcγRIII A and FcγRIII B. FcγRIII A (AAH17865.1, GenBank) has a transmembrane structure and is mainly distributed in macrophages, NK cells and eosinophilic granulocytes, in which macrophages have a high expression level of FcγRIII A, while mononuclear cells have a lower expression level. FcγRIII A relates to disulfide bond-linked CD3 or FccR I γ chain dimer, in which FcγRIII A relates to CD3 complex γ chain on macrophages, while FcγRIIIA relates to chain on NK/LGL.

As used herein, the term "FcRn" is neonate Fc receptor (P61769, UniProtKB/Swiss-Prot), which is a heterologous dimer consisting of a large subunit and a small subunit, the large subunit has a molecular weight of 45-53 kD, called as α chain; the small subunit is (32 microglobulin (β2m), has a molecular weight of 14 kD, called as β chain, the two chains are bound together in a non-covalent bond form. When physiologic pH is 7.4, FcRn does not bind to IgG, but under condition of endosome acidic pH 6-6.5, affinity of FcRn to IgG Fc ranges from nanomoles to micromoles.

As used herein, the term "Her2" refers to Her2 in full-length (NP 004439.2), or extracellular fragments or domains I, II, III or IV of Her2, or fragments containing at least one of them; or comprises a fusion proteins containing a Her2 extracellular fragment. However, those skilled in the art would understand that the amino acid sequence of Her2 may have a naturally generated or artificially introduced mutation or variation (including but not being limited to replacement, deletion and/or addition) without influencing its biological function. Hence, in the present invention, the term "Her2" should include any one of these sequences.

As used herein, the term "host cell" refers to a cell into which a vector can be introduced, which includes but is not limited to, for example, prokaryotic cells such as *E. coli* or *Bacterium subtilis*, fungus cells such as yeast cells or *Aspergillus*, insect cells such as S2 fruit fly cells or Sf9 cells, or animal cells such as fibroblasts, CHO cells, COS cells, NSO cells, Hela cells, BHK cells, HEK293 cells or human cells.

As used herein, the term "$K_D$" refers to a dissociation equilibrium constant for a specific antibody-antigen interaction, which is used to describe binding affinity between the antibody and the antigen.

As used herein, the term "pharmaceutically acceptable carrier and/or excipient" refers to a carrier and/or excipient pharmacologically and/or physiologically compatible to a subject and an active component, for example, see Remington's Pharmaceutical Sciences. Edited by Gennaro A R, 19th ed. Pennsylvania: Mack Publishing Company, 1995. A pharmaceutically acceptable carrier includes but is not limited to: pH regulators, surfactants, adjuvants, ion strength enhancers. For example, pH regulators include but are not limited to phosphate buffer solutions; surfactants include but are not limited to cationic, anionic or nonionic surfactants, for example, Tween-80; ion strength enhancers include but are not limited to sodium chloride.

As used herein, the term "specifically binding" refers to a non-random binding reaction between two molecules, for example, a reaction between an antibody and its antigen.

As used herein, the term "vector" refers to a nucleic acid vector that can be used for inserting polynucleotide. When a vector enables an inserted polynucleotide to express a protein encoded thereby, the vector is called as expression vector. Vector can be introduced into a host cell by transformation, transduction or transfection, so that a genetic material element carried by the vector is expressed in the host cell. Vectors are well-known by those skilled in the art, including but not being limited to: plasmids, phasmids, cosmids, artificial chromosomes, for example, yeast artificial chromosomes (YAC), bacterial artificial chromosomes (BAC) or P1-sourced artificial chromosomes (PAC); phages such as λ phages or M13 phages and animal viruses. The animal viruses usable as vectors include but are not limited to retroviruses (including lentiviruses), adenoviruses, adeno-associated viruses, herpes viruses (e.g., herpes simplex virus), poxviruses, baculoviruses, papillomaviruses, papovaviruses (e.g., SV40). A vector can contain a plurality of expression-controlling elements, including but not being limited to promoter sequence, transcription initiation sequence, enhancer sequences, selection element and reporter gene. In addition, vector may further contain replication initiation site.

Description

The present invention is directed to a humanized bispecific anti-Her2 antibody or a bispecific antigen-binding fragment thereof, comprising one antigen binding site containing variable regions of heavy and light chain of trastuzumab, and another antigen binding site containing variable regions of heavy and light chain of pertuzumab. The bispecific antibody recognizes Her2 extracellular domains IV and II.

The anti-Her2 antibody or antigen-binding fragments of the present invention comprises a first heavy chain and a first light chain relating to trastuzumab, and a second heavy chain and a second light chain relating to pertuzumab.

The first heavy chain comprises a $V_H$ having CDRs of which the amino acid sequences are shown in SEQ ID NOs: 1-3, and a $C_H$ having an amino acid sequence as shown in SEQ ID NO: 7. In one embodiment, the non-CDR region is derived from a human antibody.

The second heavy chain comprising a $V_H$ having CDRs of which the amino acid sequences are shown in SEQ ID NOs: 4-6, and a $C_H$ having an amino acid sequence as shown in SEQ ID NO: 8. In one embodiment, the non-CDR region is derived from a human antibody.

In the first heavy chain,

CDR1:
(SEQ ID NO: 1)
GFNIKDTY

CDR2:
(SEQ ID NO: 2)
IYPTNGYT

CDR3:
(SEQ ID NO: 3)
SRWGGDGFYAMDY.

In the second heavy chain,

CDR1:
(SEQ ID NO: 4)
GFTFTDYT

CDR2:
(SEQ ID NO: 5)
VNPNSGGS

CDR3:
(SEQ ID NO: 6)
ARNLGPSFYFDY.

Constant region of the first heavy chain (SEQ ID NO: 7):

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLSC

AVKGFYPSDIAVEWESNGQPENNYKTTPPVLDSDGSFFLVSKLTVDKSRW

QQGNVFSCSVMHEALHNHYTQKSLSLSPGK

Constant region of the second heavy chain (SEQ ID NO: 8):

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLWC

LVKGFYPSDIAVEWESNGQPENNYKTTPPVLDSDGSFFLYSKLTVDKSRW

QQGNVFSCSVMHEALHNHYTQKSLSLSPGK

In one embodiment, the first heavy chain $V_H$ has an amino acid sequence as shown below:

(SEQ ID NO: 9)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS

The second heavy chain $V_H$ has an amino acid sequence as shown below:

(SEQ ID NO: 10)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSS

The anti-Her2 antibody or antigen-binding fragments thereof further comprises a first light chain and a second light chain.

The first light chain comprising a $V_L$ having CDRs of which the amino acid sequences are shown in SEQ ID NOs: 11-13. In one embodiment, the non-CDR region is derived from a human antibody.

The second light chain comprising a $V_L$ having CDRs of which the amino acid sequences are shown in SEQ ID NOs: 14-16. In one embodiment, the non-CDR region is derived from a human antibody.

In the first light chain,

CDR1:
(SEQ ID NO: 11)
QDVNTA

CDR2:
(SEQ ID NO: 12)
SASFLYS

CDR3:
(SEQ ID NO: 13)
QQHYTTPPT.

In the second light chain,

CDR1:
(SEQ ID NO: 14)
QDVSIG

CDR2:
(SEQ ID NO: 15)
SASYRYT

CDR3:
(SEQ ID NO: 16)
QQYYIYPYT.

In one embodiment of the present invention, the first light chain $V_L$ has an amino acid sequence as shown below:

(SEQ ID NO: 17)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIK

The second light chain $V_L$ has an amino acid sequence as shown below:

(SEQ ID NO: 18)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIK

The present invention is directed to a humanized bispecific anti-Her2 antibody or an antigen binding fragment thereof, comprising: a first heavy chain comprising a variable region ($V_H$) having an amino acid sequence of SEQ ID NO: 9, a first light chain comprising a variable region ($V_L$) having an amino acid sequence of SEQ ID NO: 17, a second heavy chain comprising a variable region ($V_H$) having an amino acid sequence of SEQ ID NO: 10, and a second light chain comprising a variable region ($V_L$) having an amino acid sequence of SEQ ID NO: 18, wherein the first $V_H$ and the first $V_L$ form a first antigen binding site specific for extracellular domain IV of HER2, and the second $V_H$ and the second $V_L$ form a second antigen binding site specific for extracellular domain II of HER2.

In one embodiment of the present invention, the anti-Her2 antibody or an antigen binding fragment thereof further comprises a first light chain $C_H$ and/or a second light chain $C_H$ having an amino acid sequence of SEQ ID NO: 19:

(SEQ ID NO: 19)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

In one embodiment of the present invention, the anti-Her2 antibody or an antigen binding fragment thereof comprises a first heavy chain having an amino acid sequence as SEQ ID NO: 22, wherein the underlined part is amino acid sequence of heavy chain variable region:

(SEQ ID NO: 22)
EVQLVESGGGLVQPGGSLRLSCAASGFNIKDTYIHWVRQAPGKGLEWVAR

TYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLSCAVKGFYPSDIAVEWESNGQPENNYKTTPPV

LDSDGSFFLVSKLTVDKSRWQQGNVFSCSVMHEALHNHYTQKSLSLSPGK

In one embodiment of the present invention, the anti-Her2 antibody or an antigen binding fragment thereof comprises a first light chain having an amino acid sequence as SEQ ID NO: 23, wherein the underlined part is amino acid sequence of light chain variable region:

(SEQ ID NO: 23)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In one embodiment of the present invention, the anti-Her2 antibody or an antigen binding fragment thereof comprises a second heavy chain having an amino acid sequence SEQ ID NO: 25; wherein the underlined part is amino acid sequence of heavy chain variable region:

(SEQ ID NO: 25)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLWCLVKGFYPSDIAVEWESNGQPENNYKTTPPVL

DSDGSFFLYSKLTVDKSRWQQGNVFSCSVMHEALHNHYTQKSLSLSPGK

In one embodiment of the present invention, the anti-Her2 antibody or an antigen binding fragment thereof comprises a second light chain having an amino acid sequence SEQ ID NO: 26, wherein the underlined part is amino acid sequence of light chain variable region:

(SEQ ID NO: 26)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In one embodiment of the present invention, the anti-Her2 antibody or an antigen binding fragment thereof, contains fucose glycotype ≤25%, ≤20%, ≤15%, ≤10%, ≤8%, ≤6%, ≤5%, ≤4%, ≤3%, ≤2%, ≤1.5%, or ≤1.1% of the total saccharides that are attached to the Fc region of the antibody. The content of fucose glycotype is obtain by summing contents of all fucose-containing glycotypes, e.g., determined by N-saccharide determination method.

In one embodiment of the present invention, the anti-Her2 antibody or an antigen binding fragment thereof binds to Her2 protein with an EC50 of less than about 100 nM, for example, less than about 10 nM, 1 nM, 0.9 nM, 0.8 nM, 0.7 nM, 0.6 nM, 0.5 nM, 0.4 nM, 0.3 nM, 0.2 nM, 0.1 nM or less. The EC50 may be determined by Biacore method.

The bispecific antibody of the present invention combines pertuzumab and trastuzumab, and benefits from more complete blocking of the Her2-mediated signal transduction. Trastuzumab inhibits the formation of Her2 homodimerization and prevents the extracellular domain of Her2 undergoing proteolytic cleavage to form constitutively active p95 proteins; Pertuzumab blocks Her2 heterodimer formation and then completely blocks Her2-mediated signal transduction. When used alone, pertuzumab and trastuzumab do not have CDC activity. However, the bispecific antibody of the present invention exhibits strong CDC activity as observed in at least one in vitro cell based assay.

The bispecific antibody of the present invention targets different Her2 epitopes, which enhances its tumor suppressive effects and achieves a synergistic effect, and enhances the ADCC function.

In one embodiment, the bispecific antibody of the present invention lacks core fucose residue from the Fc N-glycans, and exhibits strong ADCC at low concentrations. This is because afucosylated antibody enhances its binding affinity with the Fc gamma receptor IIIa (FcγRIIIa) on the natural killer (NK) cells, and hence increases the antibody's ADCC activity. At the same time, afucosylated antibody can suppress the inhibitory effect from human immunoglobulin G (IgG) in serum for binding to the Fc gamma receptor IIIa (FcγRIIIa) on the natural killer (NK) and macrophage cells as the latter's binding affinity with FcγRIIIa is much weaker.

Removal of the core fucosylation to increase the antibody affinity with FcγRIIIa is one of the most effective ways to increase ADCC. Most therapeutic antibodies currently on the market are heavily fucosylated because they are produced by mammalian cell lines such as Chinese Hamster ovary (CHO) with intrinsic enzyme activity responsible for the core-fucosylation of the Fc N-glycans of the products. The present invention provides a CHO mutant that does not have a functional Slc35C1 gene, i.e., the CHO mutant has a dysfunctional Slc35C1 gene, which encodes the GDP-fucose transporter SLC35C1 that critically regulates the fucosylation of glycans. In one embodiment, the CHO mutant cell line does not contain a mutation that affects the regulation of sialic acids; i.e., the CHO mutant does not contain a dysfunctional gene that affects the production of sialic acids. In another embodiment, the CHO mutant of the present invention only contains one dysfunctional gene from CHO that affects the regulation of glycan, i.e., the Slc35C1 gene is knocked out. The CHO mutant does not contain any other dysfunctional gene (other than the Slc35C1 gene) that affects the regulation of glycans.

The SLC35C1-deficient CHO cells of the present invention produce antibody with fucose content about ≤10%, ≤8%, ≤6%, ≤4%, ≤3%, ≤2%, ≤1.5%, or ≤1.1% of the total saccharides that are attached to the Fc region of the antibody.

Figure 2:
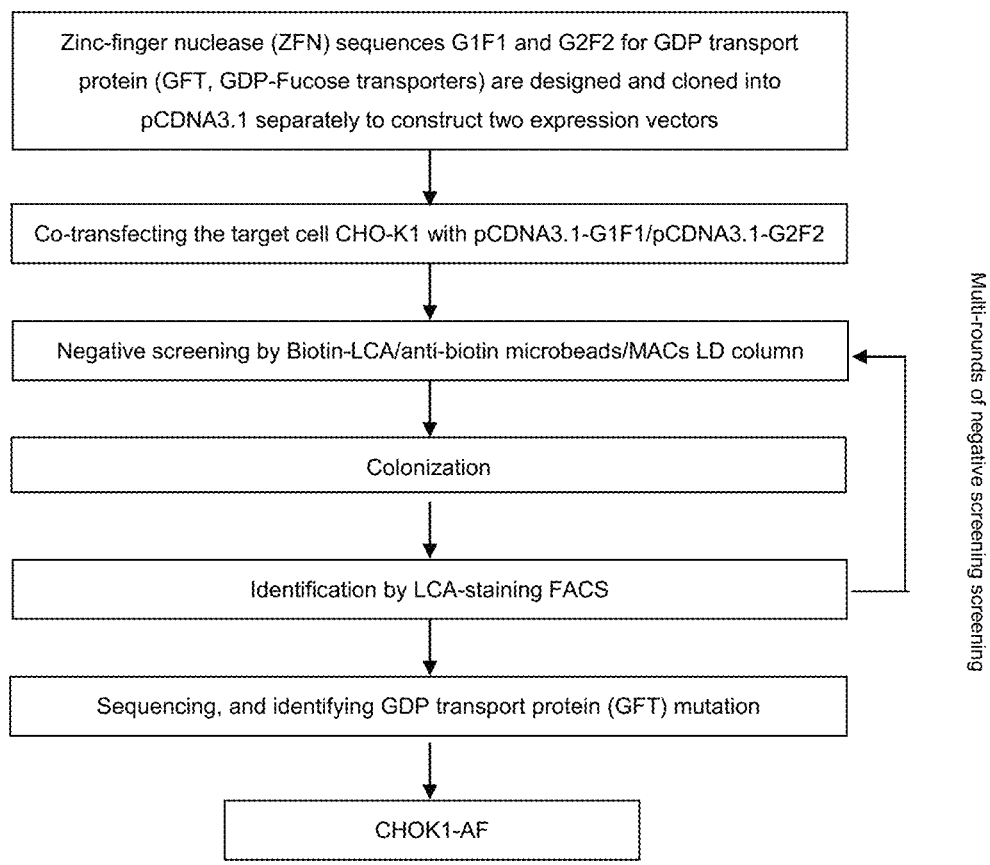
FIG. 2 shows a flow chart of the method for preparing a CHO mutant CHOK1-AF, in which the Slc35c1 gene is knocked out.

The present invention provides a method to produce mutant SLC35C1-deficient CHO cells. The method uses the zinc finger enzyme knock-out technique to knock out the key fucose-modified protein GFT (GDP-fucose transporter) in the host CHO cells, and thus the fucosylated level of the antibody produced is effectively reduced. This method can block both the classical and the compensatory pathways of fucosylation, so the method is effective in reducing fucosylation. The method comprises using zinc-finger nuclease technique to design two GFT zinc-finger nucleases for GFT gene Slc35c1 sequence (GenBank: BAE16173.1); the two zinc-finger nucleases are designed to bind double-stranded DNA of the target gene separately. The two zinc-finger nuclease sequences for GFT are cloned to construct two expression vectors. The two expression vectors are co-transfected into the target CHO cells by a suitable method known to a skilled person, e.g., by electrotransfection technique. After transfection, the transfected cells are cultivated, performed passage and amplification. The clones without fucosylation modification are selected via multi-turns of negative separation and clonal culture. One specific method is illustrated in FIG. 2.

The present invention provides a method to remove the core fucosylation of the bispecific antibody, which improve the ADCC effect of the antibody. In the present method, the bispecific antibody is produced using a CHO mutant that has a dysfunctional Slc35C1 gene, e.g. CHOK1-AF, which results in the core-fucose level of less than 1.5%. The MBS301 of the present patent has a 10-fold increase in ADCC activity compared to MIL203/204, which does not remove the core fucose unit.

The bispecific antibody of the present invention, e.g., MBS301 is designed to bind against Her2 extracellular domains IV and II; it has higher cell direct killing activity, ADCC activity, CDC activity and the tumor suppressing ability in mice than using each antibody alone. MBS301 exhibits higher cell direct killing activity, higher ADCC activity, when compared with the combination use of trastuzumab and pertuzumab in in vitro cell line activity studies, while CDC activity is similar to the combination use of trastuzumab and pertuzumab.

In one embodiment, the bispecific antibody of the present invention is a "knob-into-hole" antibody, which has modified amino acid sequence in the CH3 region to facilitate the pairing of the heterologous half-antibodies. For example, the constant region of the first heavy chain has 3 mutations from human Fc; the mutations are T369S, L371A, and Y410V in SEQ ID NO: 7. The constant region of the second heavy chain has 1 mutation from human Fc; the mutation is T368W in SEQ ID NO: 8. The "knob-into-hole" structure antibody maintains the normal antibody structure and size and provide bifunctional activity.

In one embodiment, the present invention relates to isolated nucleic acid molecules which are capable of encoding the first and the second heavy chains and the first and the second light chain of the Her2 antibody of the present invention.

In another aspect, the present invention relates to a vector, which comprises the isolated nucleic acid of the present invention.

In another aspect, the present invention relates to a host cell, which comprises the isolated nucleic acid molecule of the present invention, or the vector of the present invention. Preferably, the host cell is CHOK1-AF cell. Preferably, in the host cell, the gene of GFT (key protein in fucose modification pathway) is site-directly knocked out. Preferably, the knockout is performed by zinc finger nuclease technique. Preferably, the SLC35c1 sequence in the gene of GFT (GenBank accession number: BAE16173.1) is site-directly knocked out. In one embodiment of the present invention, the fucose is core fucose.

In another aspect, the present invention relates to a conjugate, which comprises an anti-Her2 antibody or an antigen binding fragment thereof and a coupling part, wherein, the anti-Her2 antibody is the anti-Her2 antibody or an antigen binding fragment thereof according to any one of items of the present invention, the coupling part is a detectable label; preferably, the coupling part is a radioactive isotope, a fluorescent material, a luminescent material, a colored material or an enzyme.

In another aspect, the present invention relates to a kit, which comprises the anti-Her2 antibody or an antigen binding fragment thereof according to the present invention, or comprises the conjugate of the present invention. The kit may further comprise a second antibody, which specifically recognizes the anti-Her2 antibody or an antigen binding fragment thereof; optionally, the second antibody further comprises a detectable label, such as a radioactive isotope, a fluorescent material, a luminescent material, a colored material or an enzyme. In another aspect, the present invention relates to a use of the anti-Her2 antibody or an antigen binding fragment thereof according to the present invention or the conjugate of the present invention in manufacturing a kit, wherein the kit is used for detecting the existence of Her2 or the level of Her2 in a sample.

In another aspect, the present invention relates to a pharmaceutical composition, which comprises the anti-Her2 antibody or an antigen binding fragment thereof or the conjugate of the present invention; optionally, further comprises a pharmaceutically acceptable carrier and/or an excipient; optionally, further comprises one or more chemotherapeutic drugs or cytotoxic drugs. The chemotherapeutic drug or cytotoxic drug may be selected from: (1) drugs acting on DNA chemical structure: alkylating agent such as mechlorethamines, nitroso urines, methylsulfonic acid esters; platinum compounds such as cis-platinum, carboplatin and oxaliplatin, etc.; mitomycin (MMC); (2) drugs affecting synthesis of nucleic acids: dihydrofolate reductase inhibitors such as methotrexate (MTX) and Alimta, etc.; thymidine synthase inhibitor such as fluorouracils (5FU, FT-207, capecitabine), etc.; purine nucleoside synthase inhibitors such as 6-mercaptopurine (6-MP) and 6-TG, etc.; nucleotide reductase inhibitors such as hydroxyurea (HU), etc.; DNA polymerase inhibitors such as cytarabine (Ara-C) and Gemz, etc.; (3) drugs acting on nucleic acid transcription: drugs for inhibiting RNA synthesis by selectively acting on DNA templates, inhibiting DNA-dependent RNA polymerase, such as: actinomycin D, rubidomycin, adriamycin, epirubicin, aclacinomycin, mithramycin, etc.; (4) drugs mainly acting on microtubulin synthesis: paclitaxel, docetaxel, vinblastinum, vinorelbine, podophyllotoxins, homoharringtonine; (5) other cytotoxic drugs: asparaginase mainly inhibiting protein synthesis; hormones: antiestrogens: tamoxifen, droloxifen, exemestane, etc.; aromatase inhibitors: aminoglutethimide, lentaron, letrozole, Arimidex, etc.; antiandrogens: Flutamide RH-LH agonists/antagonists: zoladex, enantone, etc.; biological response regulators: interferons mainly inhibiting tumors via body immune functions; interleukin-2; thymosins; monoclonal antibodies: rituximab (MabThera); Cetuximab (C225); HERCEPTIN® (trastuzumab); Bevacizumab (Avastin); cell differentiation inducers such as Tretinoins; cell apoptosis inducers. The bispecific antibodies and compositions thereof as disclosed by the invention can be used in drug combinations with one or more of the aforesaid anti-tumor drugs.

In another aspect, the present invention relates to a use of the anti-Her2 antibody or an antigen binding fragment thereof of the present invention or the conjugate of the present invention in the manufacture of a medicament for prophylaxis and/or treatment and/or diagnosis of cancer; the cancer is selected from breast cancer, gastric cancer, esophagus cancer, ovarian cancer, endometrial cancer, bladder cancer, lung cancer, colon cancer, head-and-neck cancer and prostate cancer; for example, the prostate cancer is advanced prostate cancer; and the breast cancer is metastatic breast cancer.

The present invention is further directed to a method for treating cancer. The method comprises the step of administering an effective amount of the anti-Her2 antibody or an antigen binding fragment thereof of the present invention to a subject in need thereof. The cancer includes breast cancer, gastric cancer, ovarian cancer, esophagus cancer, endometrial cancer, bladder cancer, lung cancer, colon cancer, head-and-neck cancer and prostate cancer.

The pharmaceutical composition of the present invention can be applied by systemic administration or local administration. Systemic administration includes oral, parenteral (such as intravenous, intramuscular, subcutaneous, or rectal), and other systemic routes of administration. In systemic administration, the active compound first reaches plasma and then distributes into target tissues.

Dosing of the composition can vary based on the extent of the cancer and each patient's individual response. For systemic administration, plasma concentrations of the active compound delivered can vary; but are generally $1 \times 10^{-10}$-$1 \times 10^{-4}$ moles/liter, and preferably $1 \times 10^{-8}$-$1 \times 10^{-5}$ moles/liter.

Those of skill in the art will recognize that a wide variety of delivery mechanisms are also suitable for the present invention.

The present invention is useful in treating a mammal subject, such as humans, horses, and dogs. The present invention is particularly useful in treating humans.

The invention is further illustrated by the following examples.

EXAMPLES

The abbreviations/terms used in the examples are provided as follows.

MIL40: a HERCEPTIN® sample as prepared by the inventors, which is in consistence with HERCEPTIN® amino acid sequence.

MIL41: a PERJETA® sample as prepared by the inventors, which is in consistence with the amino acid sequence of PERJETA®.

MIL203: an incomplete antibody (semi-antibody), in which amino acid sequences of heavy chain and light chain are designed as Example 1.

MIL203AF: an amino acid sequence identical to MIL203, except that it is expressed in fucose-knockout engineering cell line (CHOK1-AF). In its N-saccharide modified glycotypes, the ratio of glycotypes without core fucose is ≥98.5%, i.e., the core fucose is <1.5%.

MIL204: an incomplete antibody (semi-antibody), in which amino acid sequences of heavy chain and light chain are designed as Example 1.

MIL204AF: the amino acid sequence of the Fab of MIL204AF is identical to that of MIL204, but MIL204AF is expressed in fucose-knockout engineering cell line (CHOK1-AF). In its N-saccharide modified glycotypes, the ratio of glycotypes without core fucose is ≥98.5%, i.e., the core fucose is <1.5%.

MIL203/204: a bifunctional antibody formed by assembling MIL203 and MIL204.

MBS301: a bifunctional antibody formed by assembling MIL203AF and MIL204AF.

Example 1: Amino Acid Sequence Design and Gene Sequence Optimization of Heavy Chains and Light Chains of Antibodies MIL203 and MIL204

(1) Amino Acid Sequences of MIL203 Light Chain and Heavy Chain

The heavy chain of MIL203 has the amino acid sequence of SEQ ID NO: 22.

The light chain of MIL203 has the amino acid sequence of SEQ ID NO: 23.

(2) Nucleic Acid Sequences of Light Chain and Heavy Chain of MIL203

The optimized gene sequences for encoding light chain and heavy chain of MIL203 are as follows.

MIL203 heavy chain base sequence is shown as SEQ ID NO: 20, wherein the underlined part is base sequence of heavy chain variable region.

```
(SEQ ID NO: 20)
gaggtgcagctggtggagagcggcggcggcctggtgcagcccggcggcag cctgcgcctgagctgcgccgccagcggcttcaacatcaaggatacctaca tccactgggtgcgccaggctcccggcaagggcctggagtgggtggccgc atctaccccaccaacggctacacccgctacgccgatagcgtgaagggccg cttcaccatcagcgccgataccagcaagaacaccgcctacctgcagatga acagcctgcgcgccgaggataccgccgtgtactactgcagccgctgggcc ggcgatggcttctacgccatggattactggggccagggcaccctggtcac cgtgagcagcgctagcaccaagggcccatcggtcttccccctggcaccct cctccaagagcacctctggggggcacagcggccctgggctgcctggtcaag gactacttccccgaaccggtgacggtgtcgtggaactcaggcgccctgac cagcggcgtgcacaccttcccggctgtcctacagtcctcaggactctact ccctcagcagcgtggtgactgtgccctctagcagcttgggcacccagacc tacatctgcaacgtgaatcacaagcccagcaacaccaaggtggacaagaa agttgagcccaaatcttgtgacaaaactcacacatgcccaccgtgcccag cacctgaactcctggggggaccgtcagtcttcctcttccccccaaaaccc
```

-continued
aaggacaccctcatgatctcccggacccctgaggtcacatgcgtggtggt ggacgtgagccacgaagaccctgaggtcaagttcaactggtacgtggacg gcgtggaggtgcataatgccaagacaaagccgcgggaggagcagtacaac agcacgtaccgtgtggtcagcgtcctcaccgtcctgcaccaggactggct gaatggcaaggagtacaagtgcaaggtctccaacaaagccctcccagccc ccatcgagaaaccatctccaaagccaaagggcagccccgagaaccacag gtgtacaccctgccccatcccgggaagagatgaccaagaaccaggtcag cctgagctgcgcagtcaaaggcttctatcccagcgacatcgccgtggagt gggagagcaatgggcagccggagaacaactacaagaccacgcctcccgtg ctggactccgacggctccttcttcctcgtgagcaagctcaccgtggacaa gagcaggtggcagcaggggaacgtatctcatgctccgtgatgcatgaggc tctgcacaaccactacacgcagaagagcctctccctgtctccgggtaaa MIL203 light chain base sequence is shown as SEQ ID NO: 24, wherein the underlined part is base sequence of light chain variable region:

(SEQ ID NO: 24)
gatatccagatgacccagagccccagcagcctgagcgccagcgtgggcga tcgcgtgaccatcacctgccgcgccagccaggatgtgaacaccgccgtgg cctggtaccagcagaagcccggcaaggcccccaagctgctgatctacagc gccagcttcctgtacagcggcgtgcccagccgcttcagcggcagccgcag cggcaccgatttcaccctgaccatcagcagcctgcagcccgaggatttcg ccacctactactgccagcagcactacaccaccccccccaccttcggccag ggcaccaaggtggagatcaagcgtacggtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt (3) Amino Acid Sequences of Light Chain and Heavy Chain of MIL204

The heavy chain of MIL204 has the amino acid sequence of SEQ ID NO: 25.

The light chain of MIL204 has the amino acid sequence of SEQ ID NO: 26.

(4) Nucleic Acid Sequences of Light Chain and Heavy Chain of MIL204

The nucleotide sequence of heavy chain of MIL204 is shown in SEQ ID NO: 21, wherein the underlined part is base sequence of heavy chain variable region.

(SEQ ID NO: 21)
gaggtgcagctggtggagagcggcggcggcctggtgcagccggcgcag cctgcgcctgtcctgcgccgccagcggcttcacctttaccgactacacca tggactgggtgcgccaggctcccggcaagggcctggagtgggtggccgac gtgaaccccaacagcggcggcagcatctacaaccagcgcttcaaggccg -continued
cttcaccctgagcgtggaccgcagcaagaacaccctgtacctgcagatga acagcctgcgcgcggaggacaccgccgtgtactactgcgcccgcaacctg ggccccagcttctacttcgactattgggggcagggcaccctggtcaccgt gagcagcgctagcaccaagggcccatcggtcttcccctggcaccctct ccaagagcacctctgggggcacagcggccctgggctgcctggtcaaggac tacttccccgaaccggtgacggtgtcgtggaactcaggcgccctgaccag cggcgtgcacaccttcccggctgtcctacagtcctcaggactctactccc tcagcagcgtggtgactgtgccctctagcagcttgggcacccagacctac atctgcaacgtgaatcacaagcccagcaacaccaaggtggacaagaaagt tgagcccaaatcttgtgacaaaactcacacatgcccaccgtgcccagcac ctgaactcctggggggaccgtcagtcttcctcttccccccaaaacccaag gacaccctcatgatctcccggacccctgaggtcacatgcgtggtggtgga cgtgagccacgaagaccctgaggtcaagttcaactggtacgtggacggcg tggaggtgcataatgccaagacaaagccgcgggaggagcagtacaacagc acgtaccgtgtggtcagcgtcctcaccgtcctgcaccaggactggctgaa tggcaaggagtacaagtgcaaggtctccaacaaagccctcccagccccca tcgagaaaccatctccaaagccaaagggcagccccgagaaccacaggtg tacaccctgccccatcccgggaagagatgaccaagaaccaggtcagcct gtggtgcctggtcaaaggcttctatcccagcgacatcgccgtggagtggg agagcaatgggcagccggagaacaactacaagaccacgcctcccgtgctg gactccgacggctccttcttcctctacagcaagctcaccgtggacaagag caggtggcagcaggggaacgtcttctcatgctccgtgatgcatgaggctc tgcacaaccactacacgcagaagagcctctccctgtctccgggtaaa The nucleotide sequence of light chain of MIL204 is shown in SEQ ID NO: 27, wherein the underlined part is base sequence of heavy chain variable region.

(SEQ ID NO: 27)
gatatccagatgacccagagcccctccagcctgtccgccagcgtgggcga ccgcgtgaccatcacctgcaaggccagccaggacgtgagcatcggcgtgg cctggtaccagcagaagcccggcaaggcccccaagctgctgatctacagc gcctcctaccgctacaccggcgtgccctcccgcttcagcggctccggcag cggcaccgactttaccctgaccatctccagcctgcagcccgaggactttg ccacctactactgccagcagtactacatctatccctataccttgggccag ggcaccaaggtggagatcaagcgtacggtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt

Example 2: Construction of 203 Antibody Eukaryotic Expression Vector and 204 Antibody Eukaryotic Expression Vector Expression vector pTGS-FRT-DHFR (Chinese patent ZL200510064335.0) was used, hygromycin selecting label was removed, GS (glutamine synthetase) expression box was added via PshA1 and Xho1 restriction enzyme cutting sites and used as selection markers; wherein GS cDNA could be obtained via RT-PCR from cell line CHO that expressed GS. The vector obtained by modification was named as GS vector.

Based on the GS vector, the completely synthesized light chain constant region (the constant region sequence was SEQ ID NO: 24 or the non-underlined sequence in SEQ ID NO: 27) was inserted via BsiwI and NotI restriction enzyme cutting sites; then, the completely synthesized 203 heavy chain constant region and 204 heavy chain constant region (the constant region sequences were separately non-underlined sequences in SEQ ID NO: 20 and SEQ ID NO:21) were separately inserted via Nhe I and XhoI restriction enzyme cutting sites; and after modification of constant regions, GS-203 vector containing 203 light chain constant region and heavy chain constant region and GS-204 vector containing 204 light chain constant region and heavy chain constant region were separately obtained.

The genes for 203 light chain variable region and heavy chain variable region and 204 light chain variable region and heavy chain variable region (which were separately underlined sequences in SEQ ID NO: 24, SEQ ID NO: 27, SEQ ID NO: 20 and SEQ ID NO: 21) were completely synthesized, and inserted via construction into pGEM-TEasy vector to obtain vectors separately named as pGEM-TEasy-203/Vκ vector, pGEM-TEasy-204/Vκ vector, pGEM-TEasy-203/$V_H$ vector and pGEM-TEasy-204/$V_H$ vector.

The pGEM-TEasy-203/Vκ and pGEM-TEasy-204/Vκ were separately digested with ClaI and BsiwI, to separately obtain 203 light chain variable region gene and 204 light chain variable region gene.

The GS-203 vector and GS-204 vector as above constructed were separately taken in an amount of 1 μg, and separately digested with ClaI and BsiwI.

The GS-203 vector digested with ClaI and BsiwI as above-obtained and 203 light chain variable region were linked with T4 DNA ligase; and the GS-204 vector digested with ClaI and BsiwI as above-obtained and 204 light chain variable region were linked with T4 DNA ligase. The resultant plasmids carrying 203 light chain and 204 light chain were separately named as pTGS-203Vκ vector and pTGS-204Vκ vector.

The pGEM-TEasy-203/$V_H$ and pGEM-TEasy-204/$V_H$ were separately taken and digested with EcoR I and Nhe I, to separately obtain 203 heavy chain variable region gene and 204 heavy chain variable region gene. The pTGS-203Vκ vector and pTGS-204Vκ vector were separately taken in amount of 1 μg, and separately digested with EcoR I and Nhe I. The pTGS-203Vκ digested with EcoR I and Nhe I as above obtained and 203 heavy chain variable region gene, as well as the pTGS-204Vκ and 204 heavy chain variable region gene were separately linked with T4 DNA ligase. Based on the pTGS-203Vκ and the pTGS-204Vκ, the plasmids separately carrying antibody 203 heavy chain variable region gene and antibody 204 heavy chain variable region gene were obtained, which were separately named as 203 antibody eukaryotic expression vector and 204 antibody eukaryotic expression vector.

Example 3: Fucose Knockout and Suspension Acclimatization of Host Cells

CHO-K1 cells (ATCC: 58995535) purchased from ATCC were subjected to gene knockout so that the proteins expressed by themselves nearly or completely did not have fucosylation modification, and the obtained fucose-knockout host cells were named as CHOK1-AF. Specific method comprised: modifying expression system by genetic engineering technique, in which site-specific knockout of key protein GFT for fucosylation modification route was carried out in host cell CHO-K1 for antibody expression to effectively reduce fucose modification level of antibody. This method could simultaneously block typical fucosylation mechanism and compensation mechanism, so as to achieve complete removal of fucosylation. Specific technical route was shown in FIG. 2, in which by using zinc-finger nuclease technique, two GFT zinc-finger nuclease sequences were designed for GFT gene SLC35c1 sequence (GenBank: BAE16173.1) and separately used to bind double-stranded DNA of target genes. Expression vector plasmids were correspondingly constructed, and the two plasmids were co-transfected into CHO-K1 cells by electrotransfection technique. The transfected cells were static cultivated on 6-well plate for 24 h and then transferred in 125 mL shake flask and cultured under shaking so as to perform passage and amplification in the shake flask. By using the specific affinity of saccharide-binding agglutinin LCA (*Lens culinaris* agglutinin) to protein fucosyl, the co-transfected cells were stained with biotin-LCA, negative separation was carried out by using anti-biotin microBeads and MACs LD column in combination, clonal culture was further performed, and fucose knockout level of clonal cells was determined by flow cytometry technique; and clone 1G7 without fucosylation modification was obtained via multiturns of negative separation and clonal culture.

Figure 3:
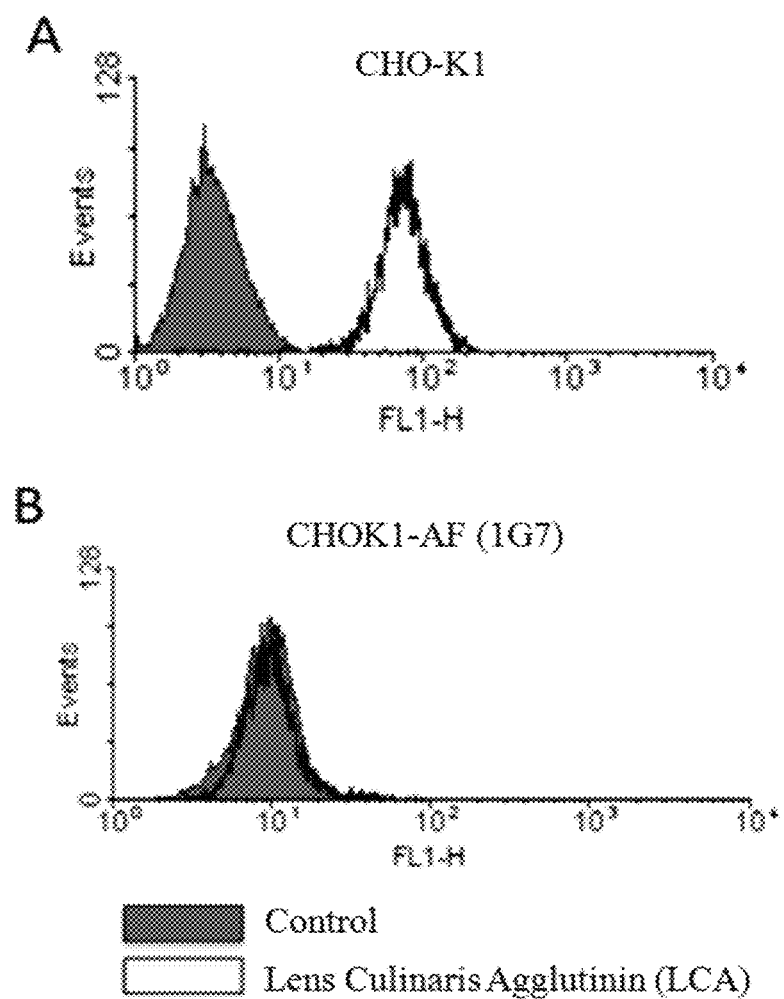
FIG. 3 shows the fucose expression level of CHO-K1 cells (A) and CHOK1-AF cells (B) determined by FACS.

FIG. 3 shows the fucose expression level of CHO-K1 cells (A) and CHOK1-AF cells (B). The dark color-filled peak refers to the control cells which do not express fucose. The black line peak represents the fucose expression level of CHO-K1 (A) or CHOK1-AF cells (B) determined by FCAS using *Lens culinaris* agglutinin (LCA) reagent, which has high specific binding affinity to the fucose unit. The results show that CHO-K1 cells express high level of fucose and CHOK1-AF cells do not express the fucose.

The CHOK1-AF cell was deposited in China General Microbiological Culture Collection Center (No. 1 West Beichen Road, Chaoyang District, Beijing 100101, China) on Jun. 14, 2017, with a deposit number of CGMCC No. 14287.

The total RNA of clone 1G7 without fucosylation modification was extracted, after reverse transcription, the gene encoding GDP transport protein was taken and sequenced to confirm that this gene was mutated successfully, and could not be normally expressed.

Further acclimatization and culture: post-thawed host cell gmt4⁻-CHO-K1 was subjected to adherent culture in seed culture medium (see: Table 1-1) (containing 10% calf serum), serum was gradually reduced (from 10%, 5%, 2.5%, 1%, 0.5%, to totally free of serum), transferred in a shake flask to perform suspension acclimatization, and passage was performed by about 10 times in total. When host cells were completely suspended and stably increased exponentially, stable host cells capable of growing in seed culture medium were finally obtained.

Example 4: Preparation of Supernatant Containing MIL203AF and MIL204AF Antibodies By using electrotransfection technique, the 203 antibody eukaryotic expression vector and 204 antibody eukaryotic expression vector obtained in Example 2 were separately transfected into target host cell CHOK1-AF, 50 μM MSX (methionine sulfoxmine) was added to seed culture medium, culture was performed at 37° C., $CO_2$ incubator for 2-4 weeks, the cells survived in this culture medium were picked out, and ELISA method was used to detect cells capable of expressing antibody. Subclone screening was performed by limiting dilution method, and after 6-8 weeks of culture and screening, monoclonal cell lines capable of effectively expressing MIL203AF and MIL204AF antibodies were obtained.

Preparation of specific culture media: the culture media were prepared according to the components as shown in Tables 1-1, 1-2 and 1-3. After being filtered under sterile condition with 0.22 μm membrane, they were used for cell culture.

TABLE 1-1

Seed culture medium

| No. | Component | Content |
|---|---|---|
| 1 | water for injection (25 ± 5° C.) | 0.9 L |
| 2 | Pluronic F-68 | 1.0 g/L |
| 3 | Glucose | 8.8 g/L |
| 4 | Culture medium powder Maxgrow 202 | 7.44 g/L |
| 5 | sodium bicarbonate | 1.98 g/L |
| 6 | sodium chloride | 3.47 g/L |
| 7 | 1M HEPES | 15 ml/L |
| 8 | 5M HCl or 5M NaOH | Regulated to pH = 7.0 ± 0.1 | diluted to 1 L

TABLE 1-2

Production culture medium

| No. | Component | Content |
|---|---|---|
| 1 | water for injection (25 ± 5° C.) | 0.8 L |
| 2 | Sodium hydroxide | 0.8 g/L |
| 3 | Culture medium powder Maxpro 302 | 11.5 g/L |
| 4 | 1 g/L vitamin B12 stock solution | 1-2 ml/L |
| 5 | 10 g/L ferrous sulfate stock solution | 0.4-0.6 ml/L |
| 6 | Sodium dihydrogen phosphate monohydrate | 0.35 g/L |
| 7 | Glucose (monohydrate) | 8.8 g/L |
| 8 | L-cysteine hydrochloride monohydrate | 0.3-0.375 g/L |
| 9 | Pluronic F-68 | 1 g/L |
| 11 | sodium chloride | 1.55 g/L |
| 12 | 5M HCl | 5.6 ml/L |
| 13 | sodium bicarbonate | 1.22 g/L |
| 14 | 1M HEPES | 7.5 ml/L |
| 15 | 5M HCl or 5M NaOH | Regulated to pH = 7.0 ± 0.1 | diluted to 1 L

TABLE 1-3

Fed-batch culture medium

| No. | Component | Content |
|---|---|---|
| 1 | water for injection (25 ± 5° C.) | 0.8 L |
| 2 | 5M NaOH | 7.325 mL |
| 3 | Anhydrous disodium hydrogen phosphate | 3.09 g/L |
| 4 | Fed-batch medium powder Maxfeed 402 | 39.03 g/L |

TABLE 1-3-continued

Fed-batch culture medium

| No. | Component | Content |
|---|---|---|
| 5 | 50 g/L L-tyrosine disodium salt dihydrate | 23.8 mL |
| 6 | 50 g/L L-cysteine hydrochloride monohydrate | 23.2 mL |
| 7 | Glucose | 50.0 g/L |
| 8 | 1.75 g/L vitamin B12 | 0.3 mL |
| 9 | 5 g/L ferrous sulfate heptahydrate | 0.3 mL |
| 10 | Pluronic F-68 | 0.3 g |
| 11 | sodium chloride | 0.24 g |
| 12 | sodium bicarbonate | 0.366 g |
| 13 | 5M HCl or 5M NaOH | Regulated to pH = 7.0 ± 0.1 | diluted to 1 L

The cell line was amplified by multi-step culture with culture media, in which seeding density was $0.5 \pm 0.2 \times 10^6$ cells/ml, passage was performed once per 2-4 days, when sufficient cells were obtained by amplification, they were transferred to fermentation culture medium (the medium comprised: production culture medium:seed culturing medium=1:1), the culture period in the fermentation culture medium was 12-14 days, and fed-batch culture medium was added in 10% volume on the $3^{rd}$, $6^{th}$, $9^{th}$ day, the supernatant was obtained after the end of culture. Thus, MIL203AF and MIL204AF were obtained, respectively.

The method for preparing MIL203 and MIL204 referred to the method for preparing MIL203AF and MIL204AF in the present example, except that the host cells were CHO-K1 cells (ATCC: 58995535) purchased from ATCC, and fucose knockout was not carried out.

Example 5: Assembling MBS301 Bispecific Antibody

1. Capture of Semi-Antibody

The supernatant of cell fermentation broth obtained in Example 4 was filtered with 0.2 μm membrane, and capture was performed by using Protein A column. Firstly, the column was balanced with low-salt Tris, pH7.5 buffer solution, then the supernatant was loaded, the column was then eluted with low-salt Tris, pH7.5 buffer solution, the column was further eluted with high-salt potassium phosphate, pH6.0 buffer solution, the column was then eluted and balanced with low-salt Tris, pH7.5 buffer solution, and finally eluted with low pH acetate buffer solution to obtain semi-antibody. The semi-antibody solution was regulated with Tris base solution to pH5.5, added with a suitable amount of Arg and preserved.

2. Assembly

The concentration of semi-antibody was determined with 280 nm absorbance using spectrophotometer. The semi-antibody was mixed in molar ratio of 1:1, regulated with Tris Base buffer solution to pH8.0, added with an amount of reducing agent GSH, reacted at 25° C. and low speed stirring overnight. The reducing agent was removed by desalting column (or ultrafiltration), and the reaction was terminated.

3. Anion (QSFF)

The sample as assembled and replaced was regulated to have pH of 8.0, conductivity of 3.5 mS/cm, filtered with 0.22 μm membrane. Firstly, an anionic chromatographic column was balanced with low-salt Tris, pH8.0 buffer solution, then the sample was loaded on the anionic chromatographic column, breakthrough component was collected, low salt Tris, pH8.0 buffer solution was then used for elution until UV280 trended to base line. The collected breakthrough sample was regulated with acetic acid solution to pH5.5.

4. Cation (50HS)

The sample as collected in the anion procedure was filtered with 0.22 μm membrane. The sample was loaded on 50HS column, then balanced with low-concentration acetate, pH5.5 buffer solution, eluted in linear gradient manner with 0-100% high-concentration acetate, pH 5.5, 20 CV, and eluted components were collected.

The obtained MBS301 antibody was used in the following examples.

Example 6: Determining Molecular Weight by Mass Spectra

1. Experimental Method

Preparation of de-sugared sample: 500 μg of MBS301 antibody was desalted with 10 kD ultrafiltration tube, added with 10 μL of G7 digestion buffer solution, 3 μL of PNGase F, diluted with ultrapure water to 100 μL, mixed homogeneously and sealed with sealing film, and placed in 37° C. water-bath overnight;

LC-MS analysis: the MBS301 or the de-sugared sample was diluted to 2.5 mg/ml, desalted with PLRP-S chromatographic column: using 10 min gradient from 95% mobile phase A (0.1% FA water), 5% mobile phase B (0.1% FA acetonitrile) to 95% mobile phase B, and maintaining for 10 min; after being desalted with reverse chromatographic column, mass spectrometry was performed with TRIPLETOF® (mass spectrometry instrument) 4600 (AB Sciex), and data were subjected to deconvolution analysis with Analyst TF1.6.

2. Experimental Results

Figure 4:
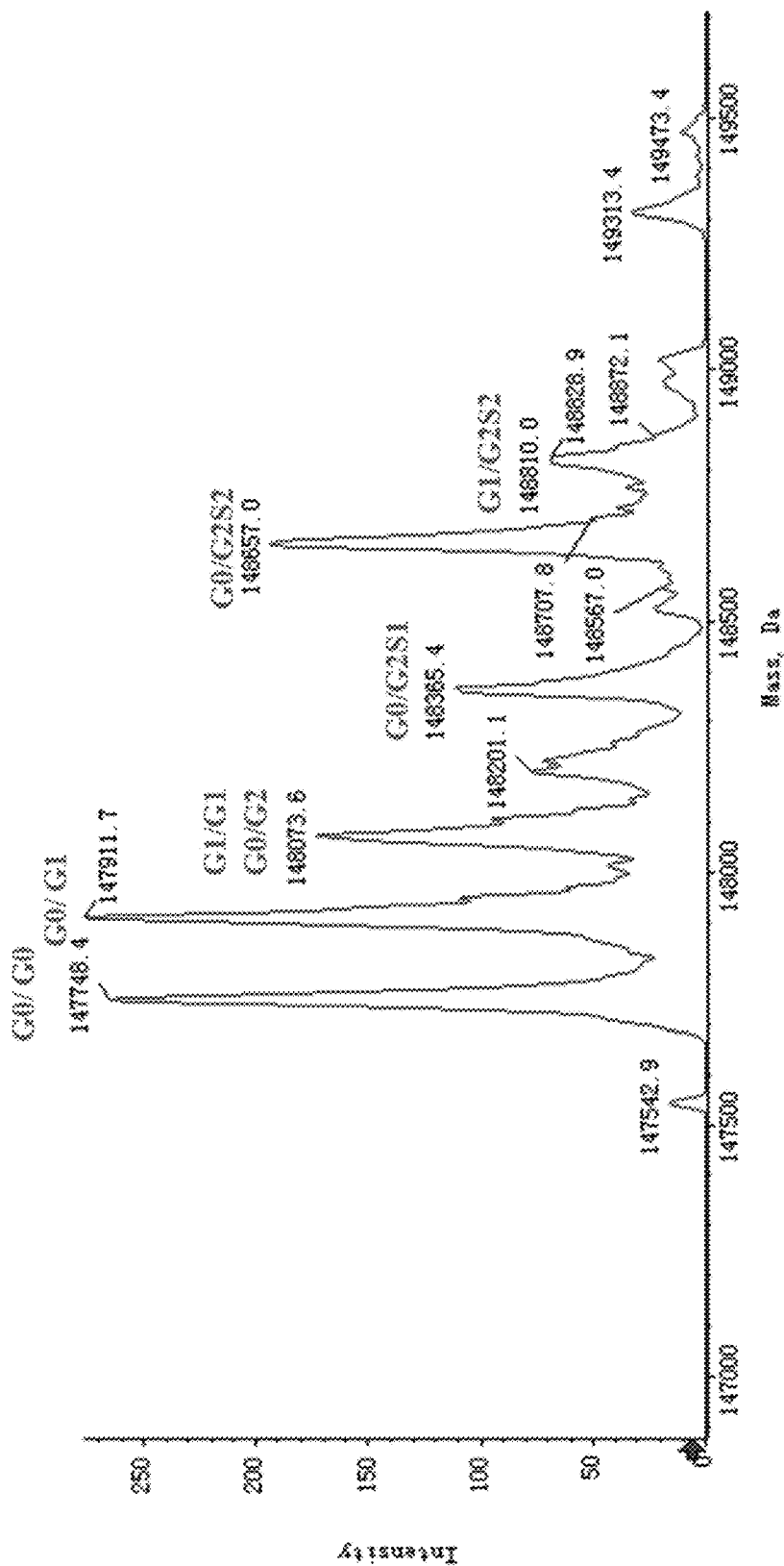
FIG. 4 shows intact molecular weight spectrum of MBS301.

The mass spectrometry results of intact protein molecular weight of MBS301 were shown in FIG. 4, MBS301 consisted of a plurality of molecules with different molecular weights, which corresponded to different glycotypes, and fucose was not found in these glycotypes.

Figure 5:
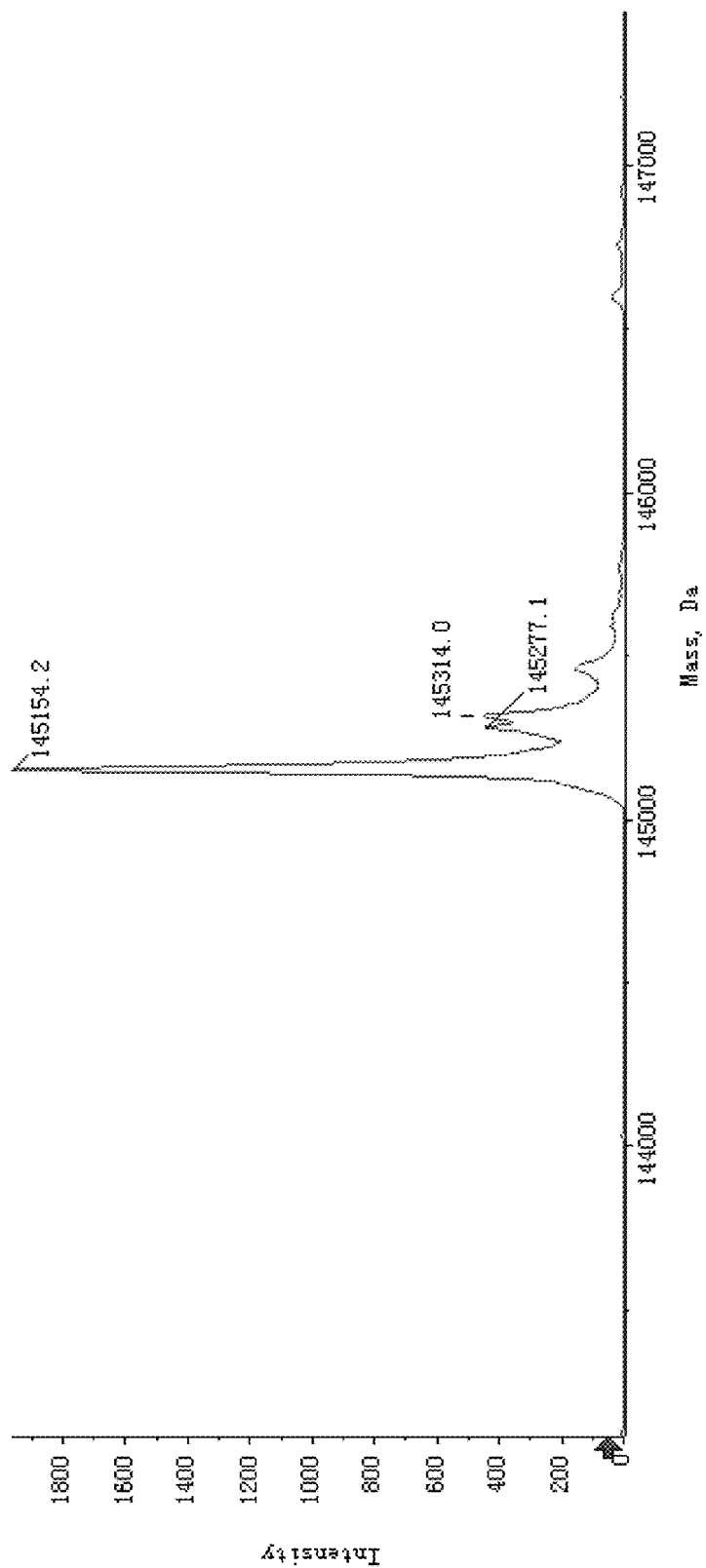
FIG. 5 shows intact molecular weight spectrum of MBS301 after N-saccharide excision modification.

After removal of N-saccharide modification, the spectrometry results of MBS301 were shown in FIG. 5, in which its intact protein molecular weight of 145,154 was in conformity with the theoretical molecular weight, which indicated that the assembly of MIL203AF and MIL204AF was successful.

Example 7: Molecular-Exclusion Chromatography (SEC-HPLC)

1. Experimental Method

Mobile phase: 0.2 mol/L potassium phosphate buffer solution, 0.25 mol/L potassium chloride, pH6.2±0.1

Preparation of sample: the sample to be tested was diluted with mobile phase to 2 mg/mL Chromatographic conditions: sample injector temperature was 6° C., sample size: 25 μl, flow rate: 0.5 ml/min, signal: 280 nm, column temperature: 30° C., isocratic elution for 30 min.

2. Experimental Results

Figure 6:
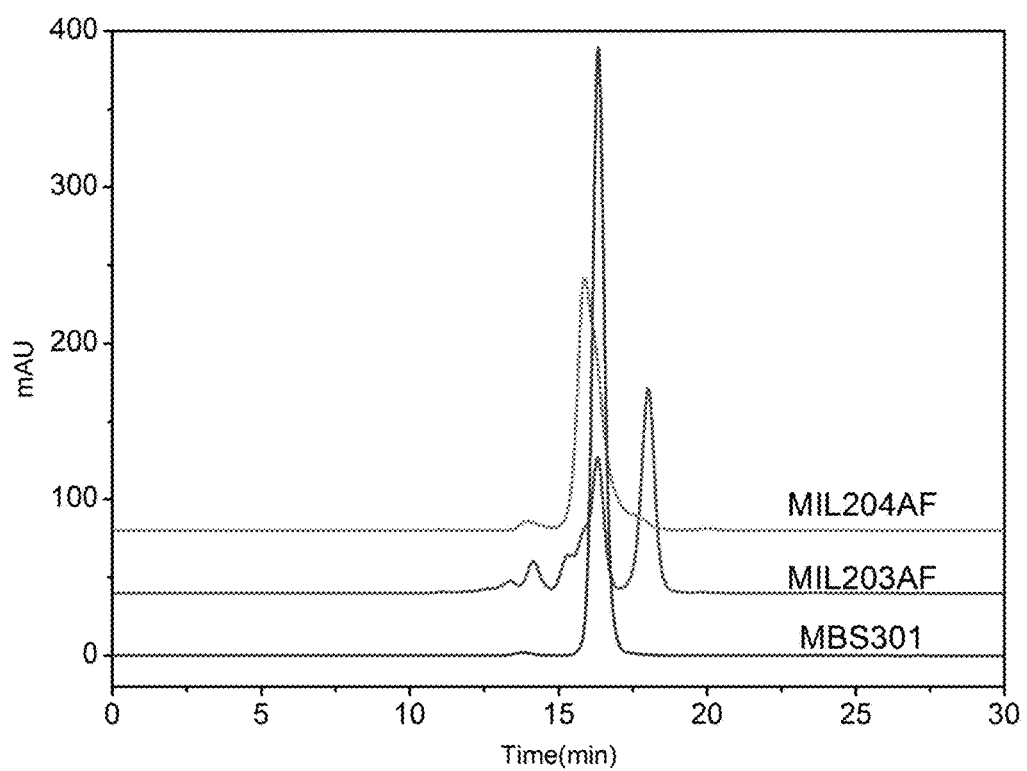
FIG. 6 shows results of SEC-HPLC analysis of MIL203AF, MIL204AF, and MBS301.

The SEC spectra of the MIL203AF, MIL204AF before assembly and the MBS301 after assembly were shown in FIG. 6. It could be seen that before assembly, MIL203AF had many semi-antibody (44.7%) and macromolecules; before assembly, MIL204AF had a broad monomer peak pattern, which indicated that their molecular sizes were not evenly distributed; however, after assembly of MBS301, the molecular size distribution pattern becomes clean, and monomer purity was 99.1%.

Example 8: N-Glycotype Analysis

1. Experimental Method:

500 μg of antibody was desalted with 10 kD ultrafiltration tube, added with 10 μL of G7 digestion buffer solution, 3 μL of PNGase F, diluted with ultrapure water to 100 μL, mixed evenly and sealed with sealing film, placed in 37° C. water-bath overnight. The digested sample was added to 300 μL of pre-cooled ethanol, mixed evenly and stood for 30 min, centrifuged at 12000 rpm for 5 min, the supernatant was taken and concentrated and dried under vacuum. DMSO and acetic acid were mixed in ratio of 350 μL:150 μL, 5 mg of 2-AB, 6 mg of Sodium Cyanoborohydride were taken and dissolved in 100 μL of the mixture solution of DMSO and acetic acid, 10 μL of the mixture solution was taken, placed in 65° C. oven, after derivation for 3 h, 200 μL of a mixture solution of 80% acetonitrile and water was added, centrifuged for 2 min, and supernatant was collected.

Chromatographic column: WATERS Acquity UPLC BEH Amide 1.7 μm, 2.1×50 mm Column;
Column temperature: 40° C.;
Excitation wavelength: λex=330 nm; λem=420 nm;
Sample size: 10 μL;

The chromatographic column was balanced with 20% mobile phase A (100 mM ammonium formate pH4.5), 80% mobile phase B (100% acetonitrile), after loading sample, the percentage of phase A was increased to 40% after 36 min.

Figure 7:
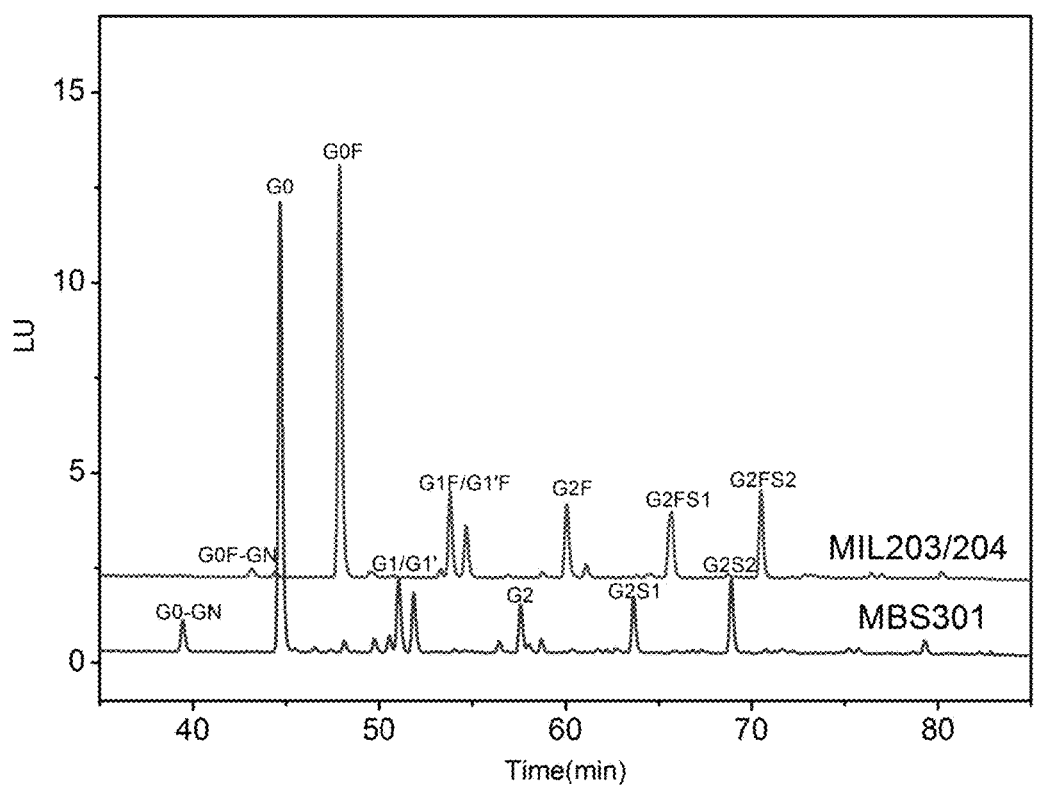
FIG. 7 shows analytic results of N-glycotypes of MIL203/204 and MBS301.
Figure 8:
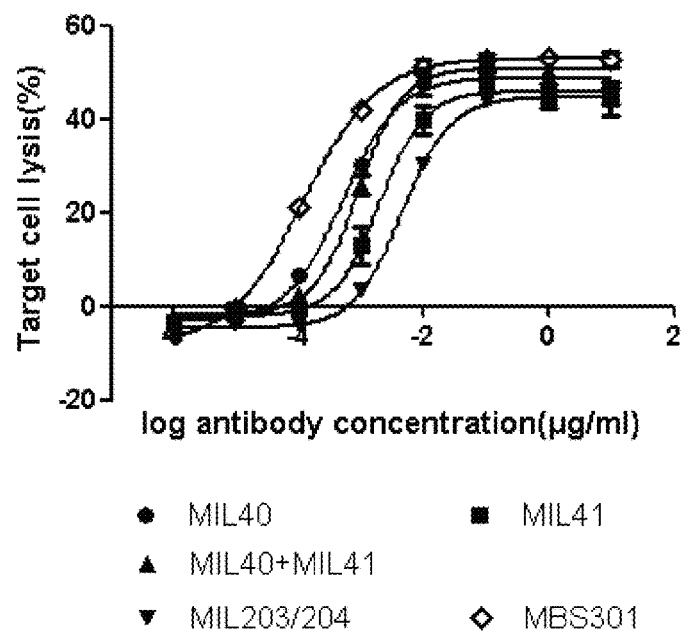
FIG. 8 shows ADCC action to SKBR-3 cells.
Figure 9:
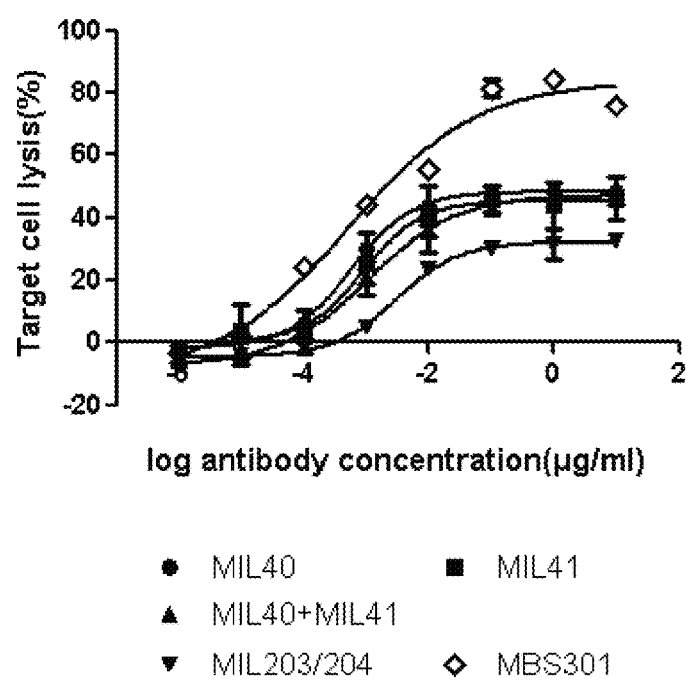
FIG. 9 shows ADCC action to BT474 cells.
Figure 10:
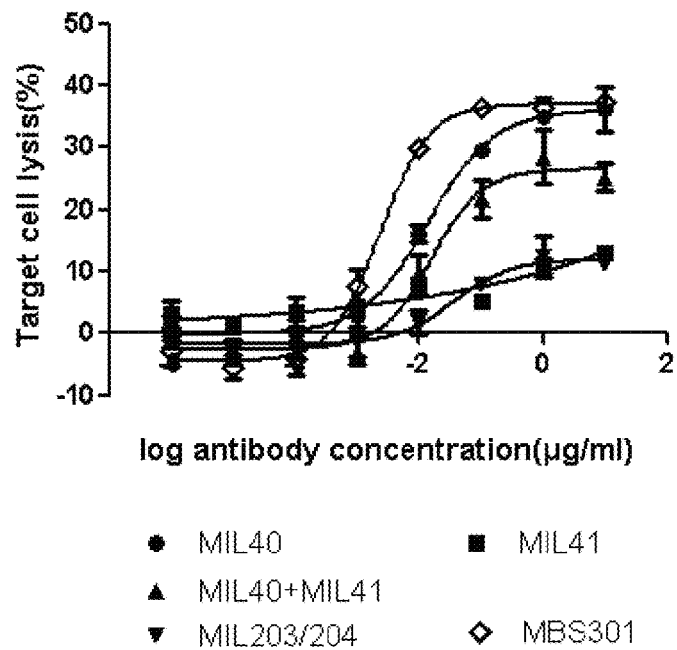
FIG. 10 shows ADCC action to SW480 cells.
Figure 11:
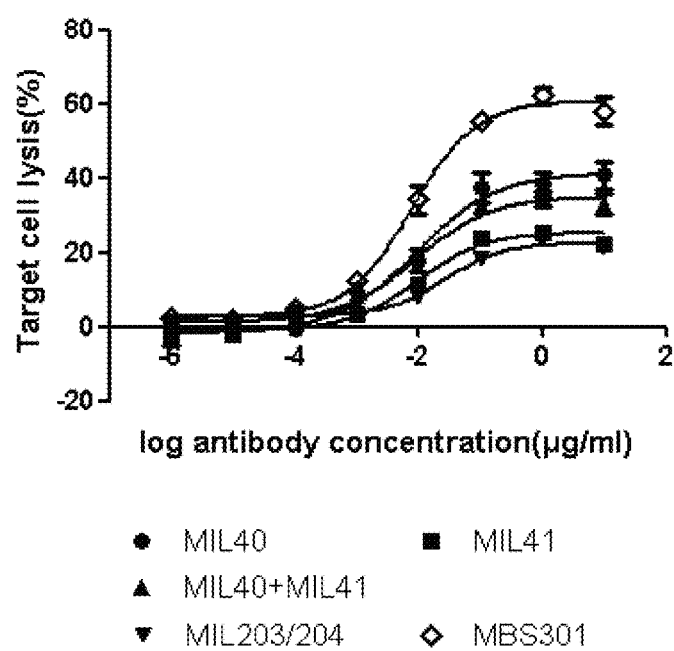
FIG. 11 shows ADCC action to HCC1419.

2. Experimental Results:

The assembled MIL203/204, MBS301 had glycotype spectra as shown in FIG. 7. It could be seen in FIG. 7 and Tables 2 and 3 that, in comparison with MIL203/204, MBS301 had a significantly decreased fucose content, and the percentage of fucose-containing glycotype G0F was only 1.1%.

TABLE 2

Percentages of glycotypes of MIL203/204 glycotypes

| Name | G0F-GN | G0 | G0F | MAN5 | G1F | G1F' | G2F | G2FS | G2FS2 |
|---|---|---|---|---|---|---|---|---|---|
| 203-204 | 1.06 | 0.62 | 44.73 | 0.98 | 9.27 | 5.87 | 8.69 | 10.53 | 9.40 |

TABLE 3

| | Percentages of glycotypes of MBS301 | | | | | | | | |
|---|---|---|---|---|---|---|---|---|---|
| Name | G0-GN | G0 | G0F | MAN5 | G1 | G1' | G2 | G2S | G2S2 |
| 203AF-204AF | 3.34 | 46.50 | 1.1 | 1.49 | 7.73 | 6.11 | 4.89 | 5.65 | 7.77 |

Example 9: Analysis of Her2 Binding Activity for Antibody

1. Experimental Method:

HBS-EP+ Buffer was used to dilute MIL40, MIL41, mixture of MIL40 and MIL41 (1:1), MIL203/204, and MBS301 samples to 0.1 μg/ml, respectively, to form ligands. HER2 (Sino Biological Inc, 10004-H08H) was diluted with HBS-EP+Buffer to 4 μg/ml, 2 μg/ml, 1 μg/ml, 0.5 μg/ml, 0.25 μg/ml and 0.125 μg/ml, to form analytes. The ligands (antibodies) were fixed by an indirect capture method, in which 25 μg/ml of Anti-Human IgG antibody (BR100839, GE) was firstly bound to surface of CMS chip via amino coupling covalent bond, then ligands and analytes were bound. Under BIACORE® (analyzers for automatically measuring and investigating the interactions of biomolecules) Wizard mode, affinity analysis experiment was performed in multi-cycle mode by separately using MIL40, MIL41, mixture of MIL40 and MIL41, and MBS301 samples as ligands, and using HER2 as analytes. The analysis for each sample comprised 3 start-up samples, 1 zero concentration control sample, 6 gradient concentration samples, and 1 repeat concentration sample, after the end of each cycle, the chip was regenerated with 3M $MgCl_2$ regenerating solution. The capture time for each concentration cycle of analyte was set as 90 s, ligand solution flow rate was 10 μl/min; the binding time for ligand and analyte was 180 s, analyte solution flow rate was 30 μl/min; dissociation time was 1200 s. The original data was introduced in BIACORE® X100 analysis software, zero concentration control was deducted, reference channel was deducted to eliminate volume effect, and 1:1 binding mode of Kinetics analysis method was used for fitting curves, and data were collated.

2. Experimental Results:

TABLE 4

The Her2 binding dynamic constants determined by Biacore technique

| Sample name | ka (1/Ms) | kd (1/s) | $K_D$ (M) |
|---|---|---|---|
| MIL40 | 3.293E+5 | 1.772E−4 | 5.383E−10 |
| MIL41 | 1.974E+5 | 2.117E−4 | 1.073E−9 |
| MIL40/MIL41 | 3.172E+5 | 1.481E−4 | 4.668E−10 |
| MIL203-204 | 3.320E+5 | 1.240E−4 | 3.735E−10 |
| MBS301 | 3.465E+5 | 1.161E−4 | 3.350E−10 |

It could be seen from the table that according to binding dynamic constants, MBS301 and MIL203/204 were superior to MIL41 in Her2 binding activity, and substantially equivalent to MIL40, and the mixture of MIL40 and MIL41 (1:1).

Example 10: Analysis of FcγRIIIa Binding Activity

1. Experimental Method:

FcγRIIIa (Sino Biological Inc, 10389-H08C1) was diluted with HBS-EP Buffer to 0.2 μg/ml, to form a ligand. HBS-EP Buffer was used for separately diluting MIL40, MIL41, mixture of MIL40 and MIL41 (1:1), MIL203/204, and MBS301 samples to 360 μg/ml, 120 μg/ml, 40 μg/ml, 13.3 μg/ml, 4.4 μg/ml, to form analytes. The ligand FcγRIIIa was fixed by indirect capture method, in which 50 μg/ml of Anti-His IgG was firstly bound to surface of CMS chip via amino coupling covalent bond, then the ligand and analyte were bound. Under Biacore Wizard mode, affinity analysis experiment was performed in multi-cycle mode by using FcγRIIIa as ligand and separately using MIL40, MIL41, mixture of MIL40 and MIL41, and MBS301 samples as analyte, respectively. The analysis for each sample comprised 3 start-up samples, 1 zero concentration control sample, 5 gradient concentration samples, and 1 repeat concentration sample, after the end of each cycle, the chip was regenerated with 10 mM Glycine-HCl, pH 1.5 regenerating solution. The capture time for each concentration cycle of analyte was set as 60 s, ligand solution flow rate was 10 μl/min; the binding time for ligand and analyte was 180 s, analyte solution flow rate was 30 μl/min; dissociation time was 180 s. The CMS chip coupled with Anti-His IgG was placed in slot, and samples were tested and analyzed. The original data was introduced in BIACORE™ X100 analysis software, zero concentration control was deducted, reference channel was deducted to eliminate volume effect, and homeostasis model assessment of affinity analysis method was used for fitting curves, and data were collated.

2. Experimental Results:

It could be seen from Table 6 that MBS301 showed the lowest $K_D$ value, which indicated that it had the strongest binding activity to FcγRIIIa, obviously stronger than that of MIL40, MIL41, mixture of MIL40 and MIL41, MIL203/204, and this exhibited the superiority of glycosylation-modified MBS301.

TABLE 5

| | $K_D$ (M) E−7 | $K_D$ (M) E−7 | $K_D$ Mean (M) E−7 |
|---|---|---|---|
| MIL41 | 8.290 | 8.059 | 8.175 |
| MIL40 | 3.194 | 3.022 | 3.108 |
| MBS301 | 1.252 | 1.096 | 1.174 |
| MIL203/204 | 5.886 | 5.852 | 5.869 |
| MIL41/MIL40 mixture | 4.312 | 4.297 | 4.305 |

Example 11: Analysis of ADCC Activity

1. Experimental method:

Target breast cancer cell SKBR-3 (purchased from ATCC, CRL-2326), effector cell NK92MI-CD16a (purchased from Huabo Bio) were centrifuged at 1200 rpm for 4 min, supernatants were discarded, ADCC experimental culture medium was used to resuspend cells, then centrifuged at 1200 rpm for 4 min, supernatants were discarded, ADCC experimental culture medium was used to resuspend cells, and the cell viability should be ≥90% according to cell counting. SKBR-3 cell density was regulated to $1.25 \times 10^5$/ml, NK92MI-CD16a cell density was regulated to $6.25 \times 10^5$/ml.

Antibodies of different concentrations were separately added to achieve final concentrations of 0.000001 μg/ml, 0.00001 µg/ml, 0.0001 µg/ml, 0.001 µg/ml, 0.01 µg/ml, 0.1 µg/ml, 1 µg/ml, 10 µg/ml, respectively, then effector cells and target cells (effector-target ratio was 5:1) were added, incubated at 37° C. for 6 h, LDH developing solution was added, 100 µL/well, stood away from light at room temperature for 20 min. Determination was performed with MD SpectraMax i3.

With regard to target breast cancer cell BT474 (purchased from ATCC, CRL-2326), colon cancer SW480 (purchased from the Cell Bank of Chinese Academy of Sciences, TCHU172), the ratio of ADCC effector cell to target cell was 10:1, that is, the target cell density was $1.25×10^5$/ml, and the effector cell density was $1.25×10^6$/ml. Other methods were the same for SKBR-3.

With regard to target breast cancer cell HCC1419 (Trastuzumab resistant, purchased from ATCC, CRL-2326), the ADCC action method was the same for SKBR-3.

Calculation of killing rate:
Background group: culture medium group
Minimum release group: target cell group
Maximum release group: target cell+lysis solution group
Experimental groups: target cell+effector cell Killing rate (%)=[(experimental group−minimum release group)/(maximum release group−minimum release group)]×100

2. Experimental Results:

FIGS. 8-11 show the results that the ADCC activities of MBS301 to different target cells were significantly superior to MIL40, MIL41, MIL40 and MIL41 administrated in combination (1:1) and MIL203/204, and killing effects depended on antibody dosage.

Example 12: Analysis for Direct Cell-Killing Activity

1. Experimental Materials

Human breast cancer BT474 cell (purchased from ATCC, HTB-20).
Human breast cancer MDA-MB-175 cell (purchased from ATCC, HTB-25).
Human breast cancer SKBR-3 cell (purchased from ATCC, HTB-30).
Human breast cancer HCC1419 cell (purchased from ATCC, CRL-2326).
Human gastric cancer NCI-N87 cell (purchased from the Cell Bank of Chinese Academy of Sciences, TCHU130).

Among these cells, BT474 was triple positive cell, Her-2 high expression; MDA-MB-175, SKBR-3 HER-2, positive, lower expression in comparison with BT474; HCC1419 was HERCEPTIN®-resistant strain.

2. Experimental Method:

Human breast cancer BT474 cells (purchased from ATCC, HTB-20) in logarithmic phase were counted, viability rate >90%, regulated to have cell density of $6.7×10^4$ cells/ml, mixed evenly, inoculated in an amount of 150 µl/well on a cell culture plate. Antibody drugs MIL40, MIL41, MIL40/MIL41 administrated in combination, MIL203/204, MBS301 were diluted then added in an amount of 50 µl/well to 96-well culture plate on which cells were spread in advance, for each antibody drug, 9 concentrations, 2.5 µg/ml, 1.25 µg/ml, 0.625 µg/ml, 0.313 µg/ml, 0.156 µg/ml, 0.078 µg/ml, 0.039 µg/ml, 0.020 µg/ml, 0.010 µg/ml, were set, and repeated wells were set for each concentration; in addition, a drug-free control group and a cell culture medium blank control group were set as well. The culture plate was placed in a cell incubator and incubated for 120 h, then 10 µl of CCK-8 solution was added to each well, after shaking, the culture plate was placed in the incubator and incubated for 3-5 h, $OD_{450}$ values were determined with ELISA. Inhibition rates of drugs to cells were calculated by the following formula:

inhibition rate=(1−(drug group $OD_{450}$−blank group $OD_{450}$)/(control group $OD_{450}$−blank group $OD_{450}$))*100%.

Human breast cancer MDA-MB-175 cells (purchased from ATCC, HTB-25) in logarithmic phase were counted, viability rate >90%, regulated to have cell density of $1×10^5$ cells/ml, mixed evenly, inoculated in an amount of 100 µl/well on a cell culture 96-well plate. For each antibody drug, 10 concentrations, 500 µg/ml, 125 µg/ml, 31.25 µg/ml, 5.208 µg/ml, 0.868 µg/ml, 0.145 µg/ml, 0.0241 µg/ml, 0.00402 µg/ml, 0.000670 µg/ml, 0.000112 µg/ml, were set. The culture plate was placed in a cell culture incubator and incubated for 72 h, and other methods were the same for BT474 cells.

Human breast cancer SKBR-3 cells (purchased from ATCC, HTB-30) in logarithmic phase were counted, viability rate >90%, regulated to have cell density of $1×10^5$ cells/ml, mixed evenly, inoculated in an amount of 100 µl/well on a 96-well plate for cell culture. For each antibody drug, 9 concentrations, 100 µg/ml, 25 µg/ml, 6.25 µg/ml, 1.56 µg/ml, 0.39 µg/ml, 0.098 µg/ml, 0.0244 µg/ml, 0.0061 µg/ml, 0.0015 µg/ml, were set. The culture plate was placed in a cell culture incubator and incubated for 120 h, and other methods were the same for BT474 cells.

Human breast cancer HCC1419 cells (purchased from ATCC, CRL-2326) in logarithmic phase were counted, viability rate >90%, regulated to have cell density of $5×10^4$ cells/ml, mixed evenly, inoculated in an amount of 100 µl/well on a 96-well plate for cell culture. For each antibody drug, 9 concentrations, 100 µg/ml, 25 µg/ml, 6.25 µg/ml, 1.56 µg/ml, 0.39 µg/ml, 0.098 µg/ml, 0.0244 µg/ml, 0.0061 µg/ml, 0.0015 µg/ml, were set. The culture plate was placed in a cell culture incubator and incubated for 120 h, and other methods were the same for BT474 cells.

Human gastric cancer NCI-N87 cells (purchased from the Cell Bank of Chinese Academy of Sciences, TCHU130) in logarithmic phase were counted, viability rate >90%, regulated to have cell density of $5×10^4$ cells/ml, mixed evenly, inoculated in an amount of 100 µl/well on a 96-well plate for cell culture. For each antibody drug, 9 concentrations, 10 µg/ml, 3.33 µg/ml, 1.11 µg/ml, 0.37 µg/ml, 0.123 µg/ml, 0.041 µg/ml, 0.0137 µg/ml, 0.0045 µg/ml, 0.0015 µg/ml, were set. The culture plate was placed in a cell culture incubator and incubated for 7 h, and other methods were the same for BT474 cells.

Figure 12:
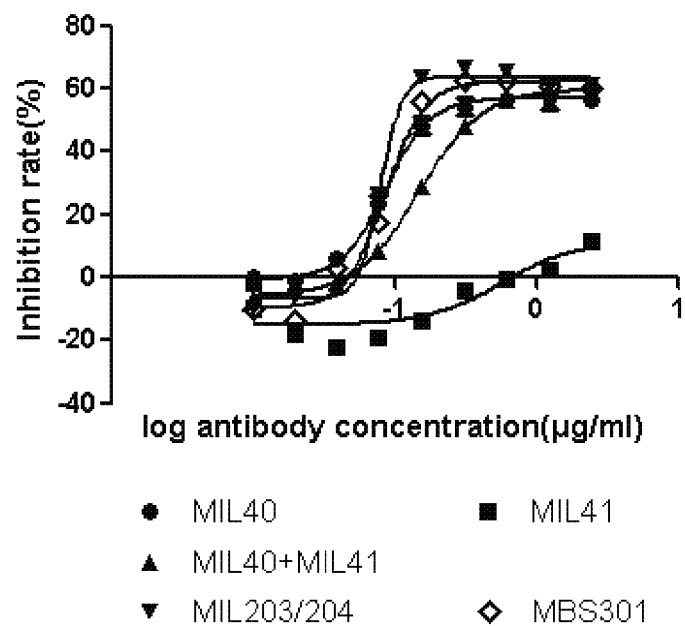
FIG. 12 shows cell direct killing effects to BT474 cells.

3. Experimental Results:

As shown in FIG. 12, MIL203/204, MBS301 had inhibition rates to BT474 cells higher than those of MIL40, MIL40/MIL41 mixture, and MIL41 had the weakest inhibition activity.

Figure 13:
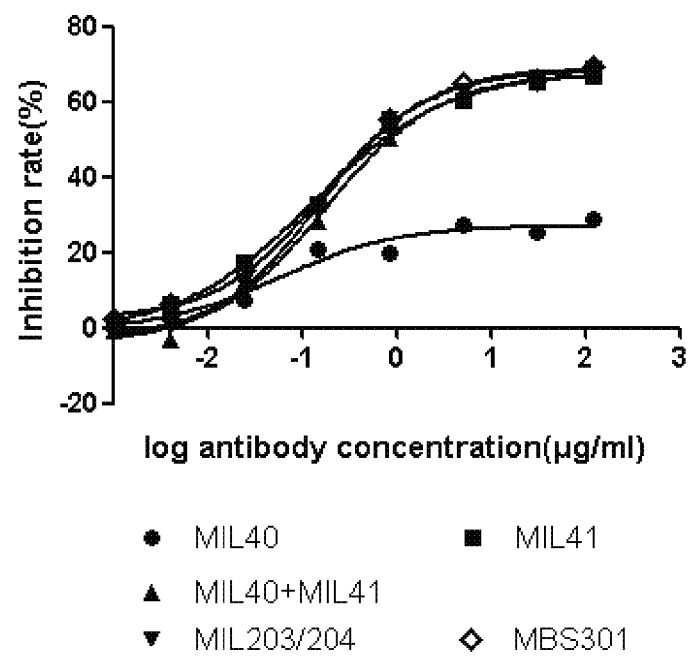
FIG. 13 shows cell direct killing effects to MDA-MB-175 cells.

As shown in FIG. 13, MIL203/204, MBS301 had inhibition rates to MDA-MB-175 cells significantly higher than that of MIL40, and very close to the inhibition rates of MIL41, MIL40/MIL41 mixture (1:1).

Figure 14:
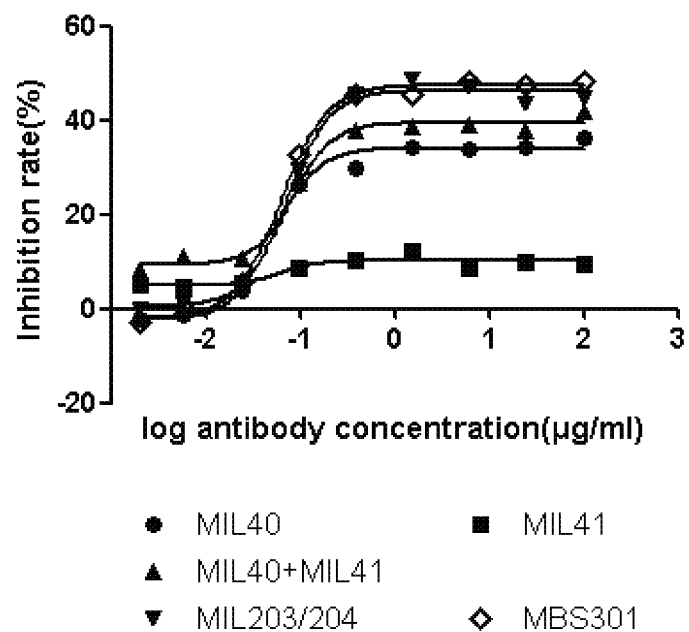
FIG. 14 shows cell direct killing effects to SKBR-3 cells.

As shown in FIG. 14, MIL203/204, MBS301 had inhibition rates to SKBR-3 cells higher than those of MIL40, MIL41, MIL40/MIL41 mixture.

Figure 15:
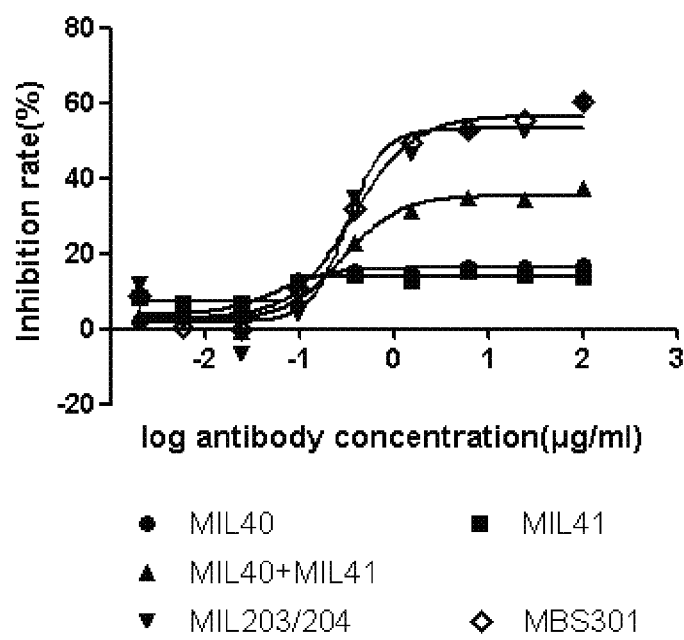
FIG. 15 shows cell direct killing effects to HCC1419 cells.

As shown in FIG. 15, MIL40, MIL41 had no significant inhibition effect to breast cancer cell HCC1419, MIL40/MIL41 administrated in combination (1:1) could inhibit cell proliferation, MIL203/204 and MBS301 showed the highest inhibition rate, and their activities were significantly superior to MIL40 and MIL41 administrated in combination (1:1).

Figure 16:
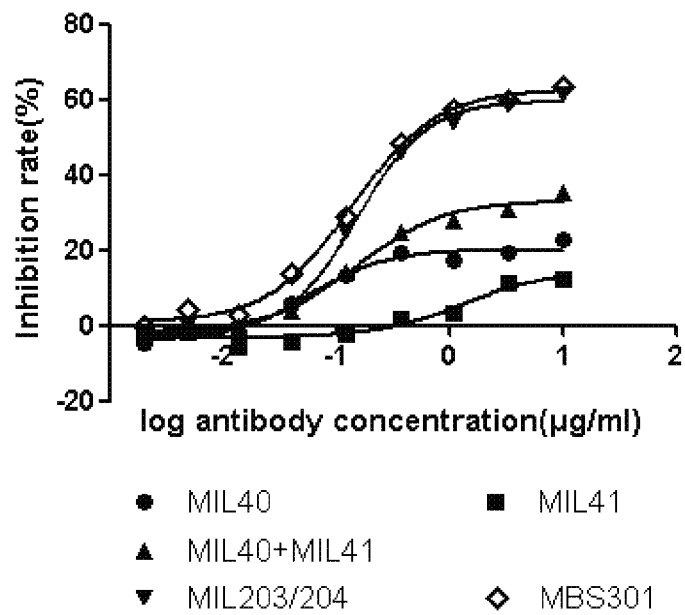
FIG. 16 shows cell direct killing effects to NCI-N87 cells.

As shown in FIG. 16, MIL40 and MIL41 administrated in combination (1:1) had inhibition effect to gastric cancer cell NCI-N87 superior to MIL40, MIL41 showed no significant inhibition effect; MIL203/204 and MBS301 showed the highest inhibition rate, and their activities were significantly superior to MIL40 and MIL41 administered in combination (1:1).

Example 13: CDC Activity

1. Experimental Method:

Target cells BT474 was centrifuged at 1200 rpm for 4 min, supernatant was discarded, the cells were resuspended with 1% FBS culture medium, counted, cell viability should be ≥90%. Cell density of BT474 cells was regulated to $2 \times 10^5$/ml, 50 µl per well.

Antibodies of different concentrations were separately added, and their final concentrations were 100 µg/ml, 25 µg/ml, 6.25 µg/ml, 1.56 µg/ml, 0.39 µg/ml, 0.098 µg/ml, 0.0244 µg/ml, 0.0061 µg/ml, respectively, 50 µl of rabbit complement (1:20 dilution) was added, incubated at 37° C. for 2 h, added with LDH developing solution, 80 µL/well, stood away from light at room temperature for 20 min. Determination was performed with MD SpectraMax i3.

Calculation of killing rate:
Background group: culture medium group
Minimum release group: target cell group
Maximum release group: target cell+lysis solution group
Experimental groups: target cell+complement Killing rate (%)=[(experimental group−minimum release group)/(maximum release group−minimum release group)]×100

Figure 17:
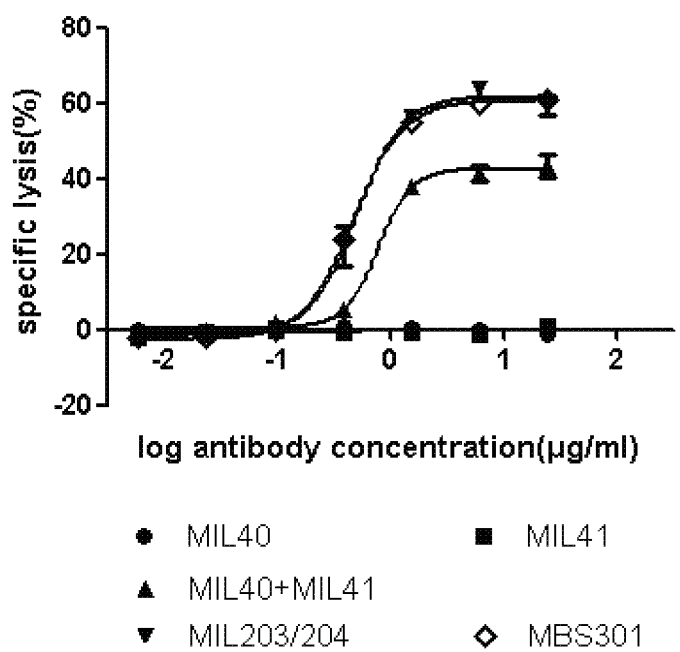
FIG. 17 shows CDC action to BT474 cells.

2. Experimental Results:

It could be seen from FIG. 17 that MIL40, MIL41 separately acted on target cell BT474 did not exhibit CDC activity, but when they were administered in combination, they showed CDC effect, bifunctional antibodies MIL203/204, MBS301 had CDC activities significantly stronger than that of MIL40 and MIL41 administered in combination, and presented antibody dose-dependent CDC killing effect.

Example 14: Analysis for Antibody FcRn Binding Activity

1. Experimental Method

FcRn (Sino Biological Inc, CT009-H08H) was diluted with HBS-EP Buffer to 0.2 µg/ml, to form a ligand. HBS-EP Buffer was used for separately diluting MIL40, MIL41, mixture of MIL40 and MIL41, MIL203/204, and MBS301 samples to 360 µg/ml, 120 µg/ml, 40 µg/ml, 13.3 µg/ml, 4.4 µg/ml, to form analytes. The ligand FcRn-His tag was fixed by indirect capture method, in which 50 µg/ml of Anti-His IgG was firstly bound to surface of CMS chip via amino coupling covalent bond, then the ligand and analytes were bound. Under Biacore Wizard mode, affinity analysis experiment was performed in multi-cycle mode by separately using FcRn as ligand, using MIL40, MIL41, mixture of MIL40 and MIL41, and MBS301 samples as analytes. The analysis for each sample comprised 3 startup samples, 1 zero concentration control sample, 5 gradient concentration samples, and 1 repeat concentration sample, after the end of each cycle, the chip was regenerated with 10 mM Glycine-HCl, pH 1.5 regenerating solution. The capture time for each concentration cycle of analyte was set as 60 s, ligand solution flow rate was 10 µl/min; the binding time for ligand and analyte was 180 s, analyte solution flow rate was 30 µl/min; dissociation time was 180 s. The CM5 chip coupled with Anti-His IgG was placed in slot, and samples were tested and analyzed. The original data was introduced in BIACORE' X100 analysis software, zero concentration control was deducted, reference channel was deducted to eliminate volume effect, and homeostasis model assessment of affinity analysis method was used for fitting curves, and data were collated.

2. Experimental Results:

It could be seen from Table 6 that MBS301 showed the lowest $K_D$ value, which indicated that it had the strongest binding activity to FcRn, significantly superior to MIL40, MIL41, mixture of MIL40 and MIL41, and substantially equivalent to MIL203/204.

TABLE 6

The FcRn binding dynamic constants determined by Biacore technique

|  | $K_D$ (M) E-7 | $K_D$ (M) E-7 | $K_D$ mean (M) E-7 |
| --- | --- | --- | --- |
| MIL41 | 5.337 | 4.495 | 4.916 |
| MIL40 | 5.891 | 5.60 | 5.746 |
| MBS301 | 1.930 | 2.128 | 2.029 |
| MIL203/204 | 2.081 | 2.059 | 2.07 |
| MIL41/MIL40 MIX | 6.050 | 4.034 | 5.042 |

Example 15: Experiment for In Vivo Tumor Suppression in Nude Mice

1. Experimental Method 6-8 week Nu/Nu nude mice, bodyweight 17.0-22.0 g, 80 female mice/batch, purchased from Beijing Vital River Experimental Animal Technology Co., Ltd., animal certificate: SCXK (Beijing)-2012-0001. The experimental animals were fed sterile IVC cages with independent air supply, 5 mice per cage. Padding material was corncob padding material (size: 4-6 mm) sterilized with $^{60}$Co radiation, the mice were fed with sterilized fodder that was specifically formulated for mice, and given purified water to drink freely. In laboratory for animal experiment, room temperature was kept around 25° C., relative humidity was kept at 40-70%, and illuminated 12 h per day.

The nude mice were hypodermically inoculated with SKO-V3. When tumor volumes were grown to be about 1500-2000 mm$^3$, tumor blocks were taken out under aseptic condition, and cut into about 1.0×1.0×1.0 mm$^3$ pieces, which was hypodermically inoculated to nude mice at axilla of right forelimb. After hypodermically inoculated tumors had sizes of 100-300 mm$^3$, they were randomly grouped according to tumor size. SKO-V3 cell culture: the cells were cultured in DMEM cell culture medium containing 10% fetal calf serum (supplemented with penicillin and streptomycin, 100 µl/ml for each), placed in a cell incubator at 37° C. and 5% CO$_2$, medium was replaced once per 1-2 days. Passage was performed by using 0.25% trypsin digestion, after centrifugation at 1000 r/min for 5 min, supernatant was discarded, and fresh culture medium was added for passage and culture.

After hypodermic transplantation, tumor-bearing animals that meet standards were selected, and randomly grouped according to tumor size, about 8 animals per group, administration was performed by caudal vein injection, twice per week, for consecutive 2 weeks.

The experimental animals were observed every day in terms of taking food, drinking water and movement, body-weight and tumor size of each animal were measured every 3 days, and the animals were executed by neck dislocation at the end of experiment, tumors visible to naked eye were stripped and weighed. All tissues obtained by dissection were placed and preserved in 4% formaldehyde for conventional pathological detection.

The data were expressed in X±s; tumor growth inhibition rate=(experimental group tumor volume−administration group tumor volume)/control group tumor volume×100%; tumor volume=½ab² (a=tumor long diameter; b=tumor short diameter);

2. Experimental Results

Figure 18:
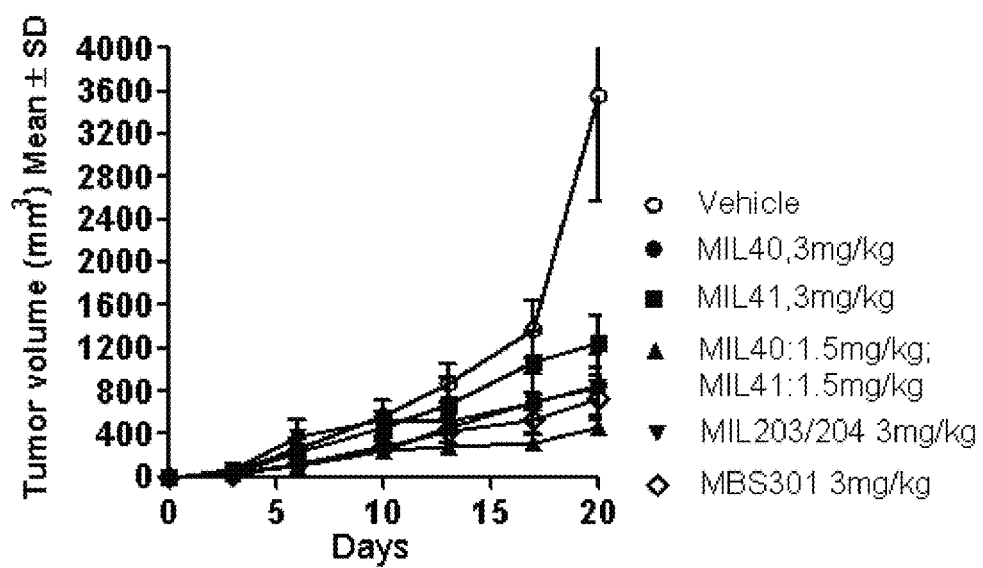
FIG. 18 shows inhibitory effect on in vivo tumor growth of human ovary cancer cells SKOV3 in nude mice.

As shown in FIG. 18, all tumors in tumor-bearing mice grew, in which tumors of control group showed progressive growth, while the growth of tumors of administration groups was slowed down to different degrees or stopped. At the end of observation period, the nude mice of control group were of drooped spirit, asarcia, skin shrinkage, and slow moving.

Tumor growth curves were plotted according to tumor sizes and time. In SKO-V3 cell tumor-bearing mice group, bifunctional antibodies MIL203/204, MBS301, and MIL40/MIL41 administrated in combination could effectively inhibit growth of SKO-V3 tumors, and their tumor inhibition abilities were superior to MIL40 and MIL41 alone.

Example 16. Anti-Her2 Bispecific Antibody MBS301 Treatment for Reducing Human Breast Tumor Volume in Mice Human Breast Cancer Cell Line BT474

This human breast cancer cell line has been established from the ductal carcinoma of a breast cancer patient. BT474 cell line was routinely cultured in DMEM medium (Gibco, America) supplemented with 10% fetal bovine serum (Gibco, America) at 37° C. in a water-saturated atmosphere at 5% $CO_2$.

Mice

Female BALB/c Nude mice; age 5-6 weeks; body weight 15-17 g (Beijing Vital River Laboratory Animal Technology Co., Ltd.); they were maintained under specific-pathogen-free condition with daily cycles of 12 h light and 12 h darkness. After arrival animals were housed in the quarantine part of the animal facility for one week to get accustomed to new environment and for observation. Food and water were provided ad libitum.

Tumor Cell Injection

At the day of injection tumor cells were harvested from culture flasks. Cell titer was adjusted to $1 \times 10^8$/ml. Before injection, 17β-ESTRADIOL pellet (Innovative Research of America) was subcutaneously implanted into the back of BALB/c nude mice. Tumor cell suspension was carefully mixed with MATRIGEL® (biological cell culture substrate) at the ratio of 1:1, then the cell suspension was 5×10e7/ml, BT474 cells were injected in a volume of 0.2 ml into the right mammary fat pad of each mouse.

Treatment

Mice were randomized for tumor volume of 125 mm³ and subsequently treated twice weekly with a volume of 10 ml/kg intravenous injection. For combination treatment MIL40 and MIL41 were given at the same time (see Table 7).

TABLE 7

| Group | No. of animals | Compound | Dose (mg/kg) | Route/Mode of administration |
|---|---|---|---|---|
| 1 | 6 | vehicle | — | i.v. twice weekly |
| 2 | 6 | MIL40 | 13.5 | i.v. twice weekly |
| 3 | 6 | MIL41 | 13.5 | i.v. twice weekly |
| 4 | 6 | MIL40 plus MIL41 | 6.75 plus 6.75 | i.v. twice weekly |
| 5 | 6 | MIL203/304 | 13.5 | i.v. twice weekly |
| 6 | 6 | MBS301 | 13.5 | i.v. twice weekly |

Figure 19:
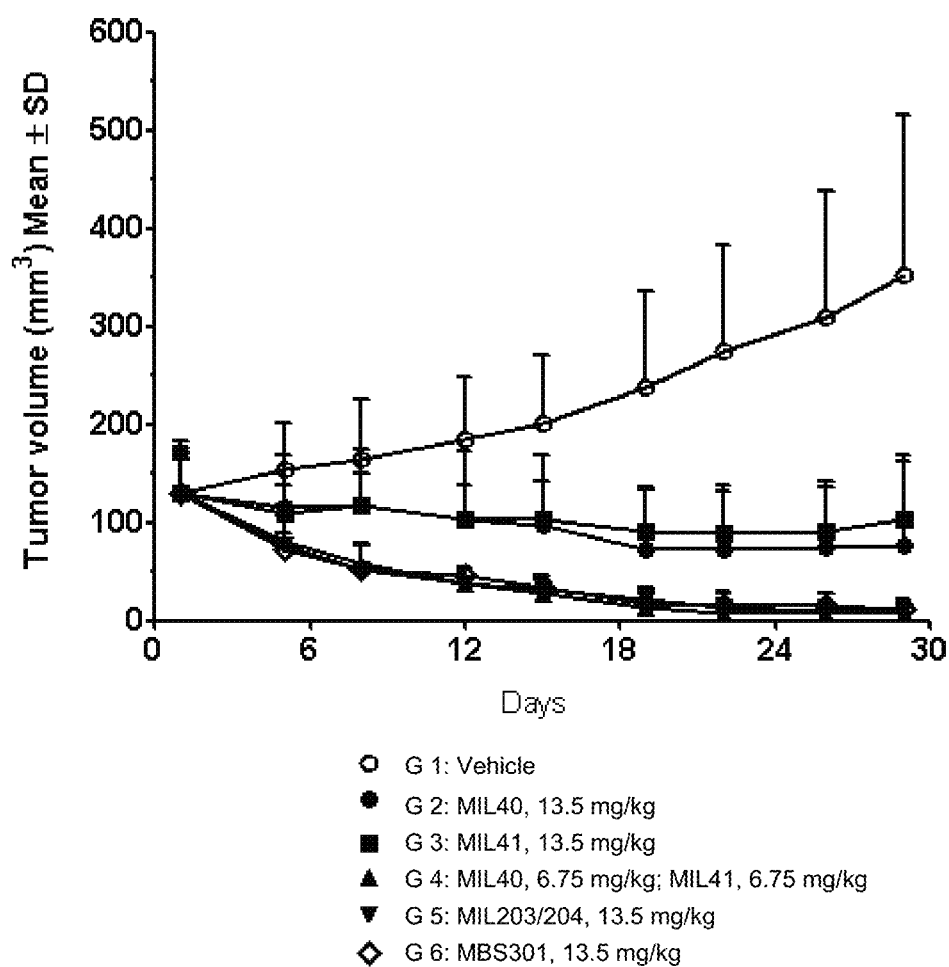
FIG. 19 shows inhibitory effects on in vivo tumor growth of human breast cancer cells BT474 in mice.

The results are shown in FIG. 19. MBS301 inhibited the growth of BT474 tumors more effectively than MIL40, as effectively as the 1:1 mixture of MIL40 with MIL41.

Example 17. Anti-Her2 Bispecific Antibody MBS301 Treatment for Reducing Human Stomach Tumor Volume in Mice Human Gastric Cancer Cell Line NCI-N87

This human stomach cancer cell has derived from metastatic site of NCI-N87 cell line was routinely cultured in 1640 medium (Gibco, America) supplemented with 10% fetal bovine serum (Gibco, America) at 37° C. in a water-saturated atmosphere at 5% $CO_2$.

Mice

Female BALB/c Nude mice; age 6-7 weeks; body weight 18-22 g (Beijing Vital River Laboratory Animal Technology Co., Ltd.); they were maintained under specific-pathogen-free condition with daily cycles of 12 h light and 12 h darkness. After arrival animals were housed in the quarantine part of the animal facility for one week to get accustomed to new environment and for observation. Food and water were provided ad libitum.

Tumor Cell Injection

At the day of injection tumor cells were harvested from culture flasks. Cell titer was adjusted to 5×10e7/ml. Tumor cell suspension was carefully mixed with Matrigel at the ratio of 1:1, then the cell suspension was 2.5×10e7/ml, NCI-N87 cells were subcutaneously injected in a volume of 0.2 ml into the right back of each mouse.

Treatment

Mice were randomized for tumor volume of 110 mm³ and subsequently treated o weekly with a volume of 10 ml/kg intravenous injection. For combination treatment MIL40 and MIL41 were given at the same time (see Table 8).

TABLE 8

| Group | No. of animals | Compound | Dose (mg/kg) | Route/Mode of administration |
|---|---|---|---|---|
| 1 | 6 | vehicle | — | i.v. once weekly |
| 2 | 6 | MIL40 | 20 | i.v. once weekly |
| 3 | 6 | MIL41 | 20 | i.v. once weekly |
| 4 | 6 | MIL40 plus MIL41 | 10 plus 10 | i.v. once weekly |

TABLE 8-continued

| Group | No. of animals | Compound | Dose (mg/kg) | Route/Mode of administration |
|---|---|---|---|---|
| 5 | 6 | MIL203/304 | 20 | i.v. once weekly |
| 6 | 6 | MBS301(=MBS301) | 20 | i.v. once weekly |

Figure 20:
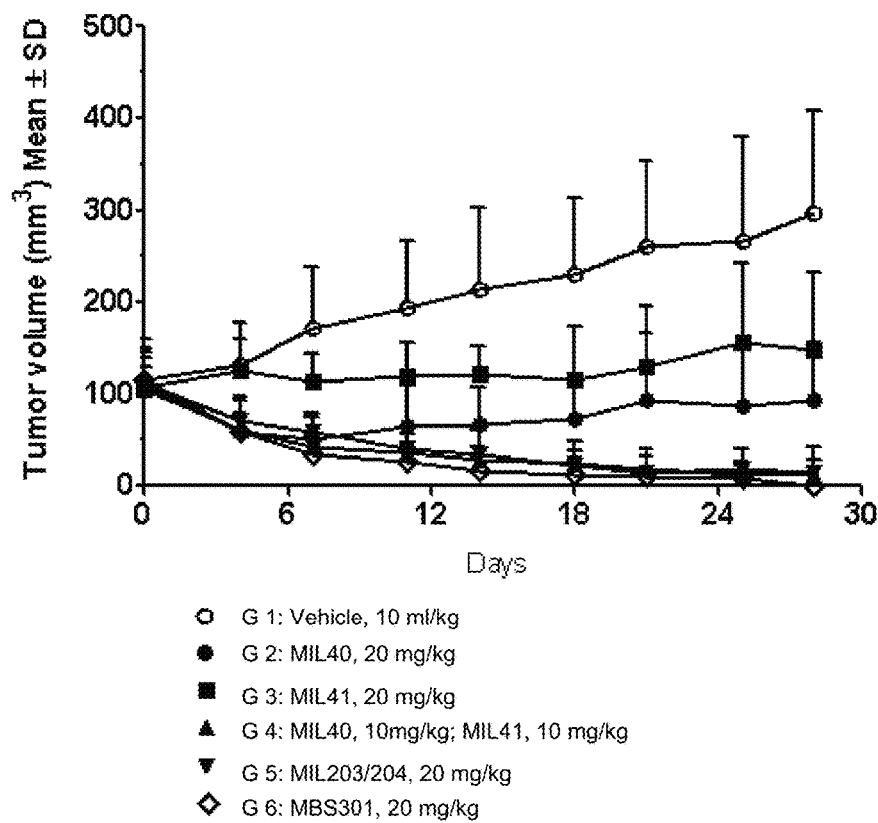
FIG. 20 shows inhibitory effects on in vivo tumor growth of human stomach cancer cells NCI-N87 in mice.

The results are shown in FIG. 20. MBS301 inhibited the growth of NCI-N87 tumors more effectively than MIL40, as effectively as MIL40 concomitant with MIL41.

In the in vivo tumor growth inhibition studies of Examples 16 and 17, both MIL40/MIL41 combination and MBS301 inhibited tumor growth, and there was no significant difference between the two groups. The additional tumor cell killing activity via ADCC of afucosylated MBS301 was not displayed in the results of Example 16 and 17; this is because humanized antibody cannot activate NK cells and macrophages of BALB/c nude mice. However, in the in vitro cell based ADCC assays, MBS301 exhibited significant enhanced ADCC activity in comparison with the mixture of MIL40 with MIL41 (see Examples 11-13, and FIGS. 8-17).

Example 18. Human Gastric Cancer GA0055 Patient Derived Xenograft (PDX) Nude Mice Model This tumor tissue has been established from the stomach of an Asian female, age 69, its pathology diagnosis was clear cell adenocarcinoma of anterior wall of gastric antrum, ulcerative type, IHC (immunohistochemistry) results was HER-2(+) with high mRNA expression level.

Mice

Female BALB/c Nude mice were maintained under specific-pathogen-free condition with daily cycles of 12 h light and 12 h darkness. After arrival, animals were housed in the quarantine part of the animal facility for one week to get accustomed to new environment and for observation. Food and water were provided ad libitum.

Tumor Inoculation

Each mouse was inoculated subcutaneously at the right flank with primary human gastric cancer model GA0055 fragment (2-3 mm in diameter) for tumor development. When average tumor size reached 146 mm$^3$, mice were randomly grouped into 3 groups (see Table 9).

TABLE 9

| Group | No. of animals | Compound | Dose (mg/kg) | Route/Mode of administration |
|---|---|---|---|---|
| 1 | 6 | vehicle | — | i.v. twice weekly |
| 2 | 6 | HERCEPTIN ® | 13.5 | i.v. twice weekly |
| 3 | 6 | MBS301 | 13.5 | i.v. twice weekly |

Figure 21:
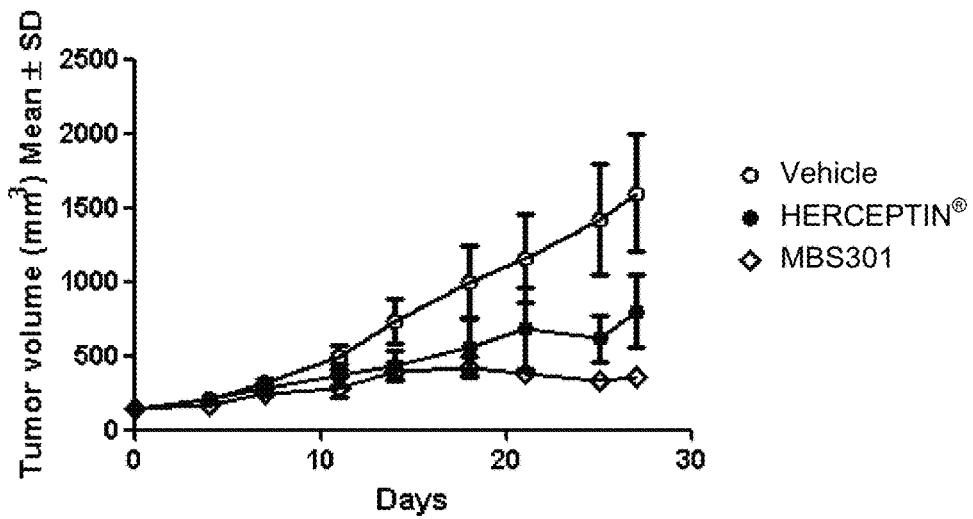
FIG. 21 shows inhibitory effects on in vivo tumor volume in a Trastuzumab-resistant stomach cancer GA055 PDX model.

In this stomach cancer PDX model, MBS301 inhibited the growth of tumors more effectively than HERCEPTIN®, the final tumor growth inhibition ratio of MBS301 is 77.82%, while Herceptin is 50.15%. After treatment for 18 days, there was significant difference in tumor size between MBS301 and Herceptin, as shown in FIG. 21.

It is to be understood that the foregoing describes preferred embodiments of the present invention and that modifications may be made therein without departing from the scope of the present invention as set forth in the claims.

What is claimed is:

1. A CHO mutant cell line having the deposit number of CGMCC No. 14287.

* * * * *

SEQUENCE LISTING

```
<160> NUMBER OF SEQ ID NOS: 27

<210> SEQ ID NO 1
<211> LENGTH: 8
<212> TYPE: PRT
<213> ORGANISM: Artificial
<220> FEATURE:
<223> OTHER INFORMATION: CDR1 of the first heavy chain

<400> SEQUENCE: 1

Gly Phe Asn Ile Lys Asp Thr Tyr
1               5

<210> SEQ ID NO 2
<211> LENGTH: 8
<212> TYPE: PRT
<213> ORGANISM: Artificial
<220> FEATURE:
<223> OTHER INFORMATION: CDR2 of the first heavy chain

<400> SEQUENCE: 2

Ile Tyr Pro Thr Asn Gly Tyr Thr
1               5

<210> SEQ ID NO 3
<211> LENGTH: 13
<212> TYPE: PRT
<213> ORGANISM: Artificial
<220> FEATURE:
<223> OTHER INFORMATION: CDR3 of the first heavy chain
```

<400> SEQUENCE: 3

Ser Arg Trp Gly Gly Asp Gly Phe Tyr Ala Met Asp Tyr
1               5                   10

<210> SEQ ID NO 4
<211> LENGTH: 8
<212> TYPE: PRT
<213> ORGANISM: Artificial
<220> FEATURE:
<223> OTHER INFORMATION: CDR1 of the second heavy chain

<400> SEQUENCE: 4

Gly Phe Thr Phe Thr Asp Tyr Thr
1               5

<210> SEQ ID NO 5
<211> LENGTH: 8
<212> TYPE: PRT
<213> ORGANISM: Artificial
<220> FEATURE:
<223> OTHER INFORMATION: CDR2 of the second heavy chain

<400> SEQUENCE: 5

Val Asn Pro Asn Ser Gly Gly Ser
1               5

<210> SEQ ID NO 6
<211> LENGTH: 12
<212> TYPE: PRT
<213> ORGANISM: Artificial
<220> FEATURE:
<223> OTHER INFORMATION: CDR3 of the second heavy chain

<400> SEQUENCE: 6

Ala Arg Asn Leu Gly Pro Ser Phe Tyr Phe Asp Tyr
1               5                   10

<210> SEQ ID NO 7
<211> LENGTH: 330
<212> TYPE: PRT
<213> ORGANISM: Artificial
<220> FEATURE:
<223> OTHER INFORMATION: constant region of the first heavy chain

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Val Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 330
<212> TYPE: PRT
<213> ORGANISM: Artificial
<220> FEATURE:
<223> OTHER INFORMATION: constant region of the second heavy chain

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 120
<212> TYPE: PRT
<213> ORGANISM: Artificial
<220> FEATURE:
<223> OTHER INFORMATION: variable region of the first heavy chain

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 10
<211> LENGTH: 119
<212> TYPE: PRT
<213> ORGANISM: Artificial
<220> FEATURE:
<223> OTHER INFORMATION: variable region of the second heavy chain

<400> SEQUENCE: 10

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Thr Asp Tyr
         20                  25                  30

Thr Met Asp Trp Val Arg Gln Ala Pro Gly Lys Gly Leu Glu Trp Val
         35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 11
<211> LENGTH: 6
<212> TYPE: PRT
<213> ORGANISM: Artificial
<220> FEATURE:
<223> OTHER INFORMATION: CDR1 of the first light chain

<400> SEQUENCE: 11

Gln Asp Val Asn Thr Ala
1               5

<210> SEQ ID NO 12
<211> LENGTH: 7
<212> TYPE: PRT
<213> ORGANISM: Artificial
<220> FEATURE:
<223> OTHER INFORMATION: CDR2 of the first light chain

<400> SEQUENCE: 12

Ser Ala Ser Phe Leu Tyr Ser
1               5

<210> SEQ ID NO 13
<211> LENGTH: 9
<212> TYPE: PRT
<213> ORGANISM: Artificial
<220> FEATURE:
<223> OTHER INFORMATION: CDR3 of the first light chain

<400> SEQUENCE: 13

Gln Gln His Tyr Thr Thr Pro Pro Thr
1               5

<210> SEQ ID NO 14
<211> LENGTH: 6
<212> TYPE: PRT
<213> ORGANISM: Artificial
<220> FEATURE:
<223> OTHER INFORMATION: CDR1 of the second light chain

<400> SEQUENCE: 14

Gln Asp Val Ser Ile Gly
1               5

<210> SEQ ID NO 15
<211> LENGTH: 7
<212> TYPE: PRT
<213> ORGANISM: Artificial
```

```
<220> FEATURE:
<223> OTHER INFORMATION: CDR2 of the second light chain

<400> SEQUENCE: 15

Ser Ala Ser Tyr Arg Tyr Thr
1               5

<210> SEQ ID NO 16
<211> LENGTH: 9
<212> TYPE: PRT
<213> ORGANISM: Artificial
<220> FEATURE:
<223> OTHER INFORMATION: CDR3 of the second light chain

<400> SEQUENCE: 16

Gln Gln Tyr Tyr Ile Tyr Pro Tyr Thr
1               5

<210> SEQ ID NO 17
<211> LENGTH: 107
<212> TYPE: PRT
<213> ORGANISM: Artificial
<220> FEATURE:
<223> OTHER INFORMATION: amino acid sequence of variable region of the
      first light chain

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 18
<211> LENGTH: 107
<212> TYPE: PRT
<213> ORGANISM: Artificial
<220> FEATURE:
<223> OTHER INFORMATION: amino acid sequence of variable region of the
      second light chain

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 19
<211> LENGTH: 107
<212> TYPE: PRT
<213> ORGANISM: Artificial
<220> FEATURE:
<223> OTHER INFORMATION: amino acid sequence of constant region of the
      first light chain or amino acid sequence of constant region of the
      second light chain

<400> SEQUENCE: 19

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 20
<211> LENGTH: 1350
<212> TYPE: DNA
<213> ORGANISM: Artificial
<220> FEATURE:
<223> OTHER INFORMATION: nucleic acid sequence encoding the first heavy
      chain

<400> SEQUENCE: 20
gaggtgcagc tggtggagag cggcggcggc ctggtgcagc ccggcggcag cctgcgcctg     60
agctgcgccg ccagcggctt caacatcaag gatacctaca tccactgggt gcgccaggct    120
cccggcaagg gcctggagtg ggtggcccgc atctacccca ccaacggcta cacccgctac    180
gccgatagcg tgaagggccg cttcaccatc agcgccgata ccagcaagaa caccgcctac    240
ctgcagatga acagcctgcg cgccgaggat accgccgtgt actactgcag ccgctggggc    300
ggcgatggct ctacgccat ggattactgg ggccagggca ccctggtcac cgtgagcagc    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgact gtgccctcta gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
```

```
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaagag   1080
atgaccaaga accaggtcag cctgagctgc cagtcaaag gcttctatcc cagcgacatc   1140
gccgtggagt gggagagcaa tgggcagccg gagaacaact acaagaccac gcctcccgtg   1200
ctggactccg acggctcctt cttcctcgtg agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350
```

<210> SEQ ID NO 21
<211> LENGTH: 1347
<212> TYPE: DNA
<213> ORGANISM: Artificial
<220> FEATURE:
<223> OTHER INFORMATION: nucleic acid sequence encoding the second heavy
      chain

<400> SEQUENCE: 21

```
gaggtgcagc tggtggagag cggcggcggc ctggtgcagc ccggcggcag cctgcgcctg     60
tcctgcgccg ccagcggctt cacctttacc gactacacca tggactgggt gcgccaggct    120
cccggcaagg gcctggagtg ggtggccgac gtgaacccca cagcggcgg cagcatctac     180 aaccagcgct tcaagggccg cttcaccctg agcgtggacc gcagcaagaa caccctgtac    240
ctgcagatga acagcctgcg cgccgaggac accgccgtgt actactgcgc cgcaacctg     300 ggccccagct tctacttcga ctattggggc cagggcaccc tggtcaccgt gagcagcgct    360
agcaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgactgtg ccctctagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc cccatcccg ggaagagatg    1080 accaagaacc aggtcagcct gtggtgcctg gtcaaaggct tctatcccag cgacatcgcc   1140
gtggagtggg agagcaatgg gcagccggag aacaactaca gaccacgcc tcccgtgctg    1200 gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 22
<211> LENGTH: 450
<212> TYPE: PRT
<213> ORGANISM: Artificial

-continued

<220> FEATURE:
<223> OTHER INFORMATION: amino acid sequence of the heavy chain of
     MIL203

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val

```
                385                 390                 395                 400
Leu Asp Ser Asp Gly Ser Phe Phe Leu Val Ser Lys Leu Thr Val Asp
                    405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 23
<211> LENGTH: 214
<212> TYPE: PRT
<213> ORGANISM: Artificial
<220> FEATURE:
<223> OTHER INFORMATION: amino acid sequence of the light chain of
      MIL203

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 642
<212> TYPE: DNA
<213> ORGANISM: Artificial
<220> FEATURE:
<223> OTHER INFORMATION: nucleic acid sequence of the light chain of
      MIL203

<400> SEQUENCE: 24
gatatccaga tgacccagag ccccagcagc ctgagcgcca gcgtgggcga tcgcgtgacc      60
```

```
atcacctgcc gcgccagcca ggatgtgaac accgccgtgg cctggtacca gcagaagccc    120
ggcaaggccc ccaagctgct gatctacagc gccagcttcc tgtacagcgg cgtgcccagc    180
cgcttcagcg gcagccgcag cggcaccgat ttcaccctga ccatcagcag cctgcagccc    240
gaggatttcg ccacctacta ctgccagcag cactacacca ccccccccac cttcggccag    300
ggcaccaagg tggagatcaa cgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 25
<211> LENGTH: 449
<212> TYPE: PRT
<213> ORGANISM: Artificial
<220> FEATURE:
<223> OTHER INFORMATION: amino acid sequence of the heavy chain of MIL204

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 26
<211> LENGTH: 214
<212> TYPE: PRT
<213> ORGANISM: Artificial
<220> FEATURE:
<223> OTHER INFORMATION: amino acid sequence of the light chain of
      MIL204

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 642
<212> TYPE: DNA
<213> ORGANISM: Artificial
<220> FEATURE:
<223> OTHER INFORMATION: nucleic acid sequence of the light chain of
      MIL204

<400> SEQUENCE: 27
gatatccaga tgacccagag cccctccagc ctgtccgcca gcgtgggcga ccgcgtgacc      60
atcacctgca aggccagcca ggacgtgagc atcggcgtgg cctggtacca gcagaagccc     120
ggcaaggccc ccaagctgct gatctacagc gcctcctacc gctacaccgg cgtgccctcc     180
cgcttcagcg gctccggcag cggcaccgac tttaccctga ccatctccag cctgcagccc     240
gaggactttg ccacctacta ctgccagcag tactacatct atccctatac cttcggccag     300
ggcaccaagg tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```